United States Patent
Prammer

(10) Patent No.: US 6,512,371 B2
(45) Date of Patent: Jan. 28, 2003

(54) SYSTEM AND METHOD FOR DETERMINING OIL, WATER AND GAS SATURATIONS FOR LOW-FIELD GRADIENT NMR LOGGING TOOLS

(75) Inventor: Manfred Prammer, Downington, PA (US), .

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/874,028

(22) Filed: Jun. 5, 2001

(65) Prior Publication Data
US 2002/0167314 A1 Nov. 14, 2002

Related U.S. Application Data

(63) Continuation-in-part of application No. 08/822,567, filed on Mar. 19, 1997, now Pat. No. 6,242,912, which is a continuation of application No. 08/542,340, filed on Oct. 12, 1995, now abandoned.

(51) Int. Cl.$^7$ .................................................. G01V 3/00
(52) U.S. Cl. ..................................................... 324/303
(58) Field of Search ................................. 324/303, 300, 324/306, 307, 309, 312, 314, 318, 322

(56) References Cited

U.S. PATENT DOCUMENTS

| | | |
|---|---|---|
| 1,158,959 A | 11/1915 | Beach |
| 2,912,641 A | 11/1959 | Ruble |

(List continued on next page.)

FOREIGN PATENT DOCUMENTS

| | | | | |
|---|---|---|---|---|
| EP | 0 295 134 A2 | 12/1988 | ............ | G01V/3/32 |
| EP | 0 581 666 A3 | 2/1994 | ............ | G01V/3/32 |
| EP | 0 649 035 B1 | 4/1995 | ............ | G01V/3/32 |
| GB | 2 056 082 A | 7/1980 | .......... | G01N/24/08 |
| WO | WO 92/10768 | 6/1992 | ............ | G01V/3/32 |
| WO | WO 98/25164 | 6/1998 | ............ | G01V/3/32 |

OTHER PUBLICATIONS

Akkurt et al., "Selection of Optimal Acquisition Parameters for MRIL Logs," SPWLA 37th Annual Logging Symposium, Jun. 16–19, 1996.
Akkurt et al., "NMR Logging of Natural Gas Reservoirs," SPWLA 36th Annual Logging Symposium (Jun. 26–29, 1995).
Brown et al., "Nuclear Magnetism Logging," Transactions of the American Institute of Mining, Metallurgical, and Petroleum Engineers, vol. 219 (1960), pp. 199–207.
Brownstein et al., "Importance of classical diffusion in NMR studies of water in biological cells," The American Physical Society, vol. 19, No. 6, (1979) pp. 2446–2453.
Cannon et al., "Quantitative NMR interpretation," Society of Petroleum Engineers, SPE 49010, 1998.

(List continued on next page.)

Primary Examiner—Louis Arana
(74) Attorney, Agent, or Firm—Bennie & Edmonds LLP

(57) ABSTRACT

A well logging system and method are disclosed for detecting the presence and estimating the quantity of gaseous and liquid hydrocarbons in the near wellbore zone. The system uses a gradient-based, multiple-frequency NMR logging tool to extract signal components characteristic for each type of hydrocarbons. To this end, new data acquisition methods are proposed in which measurements at different frequencies are interleaved to obtain, in a single logging pass, multiple data streams corresponding to different recovery times and/or diffusivity for the same spot in the formation. The resultant data streams are processed to determine mineralogy-independent water and hydrocarbon saturations and porosity estimates. Gas and oil saturations are used to obtain accurate estimates of the water content, permeability and other parameters of interest. In another aspect, a novel diffusion-enhanced data acquisition sequence is disclosed for use with low field gradient tools.

30 Claims, 23 Drawing Sheets uspat

U.S. PATENT DOCUMENTS

| | | | |
|---|---|---|---|
| 2,973,471 A | 2/1961 | Armistead et al. | |
| 3,205,477 A | 9/1965 | Kalbfell | |
| 3,213,357 A | 10/1965 | Brown et al. | |
| 3,360,716 A | 12/1967 | Bloom et al. | |
| 3,395,337 A | 7/1968 | Varian | |
| 3,402,344 A | 9/1968 | Brown et al. | |
| 3,453,433 A | 7/1969 | Alger et al. | 250/83.3 |
| 3,508,438 A | 4/1970 | Alger et al. | 73/152 |
| 3,567,935 A | 3/1971 | Naget | 250/83.1 |
| 3,567,936 A | 3/1971 | Tittman | 250/83.1 |
| 3,590,228 A | 6/1971 | Burke | 235/151.35 |
| 3,593,116 A | 7/1971 | Culpepper | 324/0.5 |
| 3,617,867 A | 11/1971 | Herzog | 324/0.5 |
| 3,638,484 A | 2/1972 | Tixier | 73/152 |
| 3,657,730 A | 4/1972 | Robinson et al. | 324/0.5 |
| 3,667,035 A | 5/1972 | Slichter | 324/0.5 R |
| 3,777,560 A | 12/1973 | Guignard | 73/151.5 |
| 3,784,898 A | 1/1974 | Darley et al. | 324/0.5 R |
| 3,896,668 A | 7/1975 | Anderson et al. | 73/152 |
| 4,291,271 A | 9/1981 | Lauffer | 324/307 |
| 4,310,887 A | 1/1982 | Suau | 364/422 |
| 4,350,955 A | 9/1982 | Jackson et al. | 324/303 |
| 4,479,564 A | 10/1984 | Tanguy | 181/105 |
| 4,528,508 A | 7/1985 | Vail, III | 324/303 |
| 4,536,714 A | 8/1985 | Clark | 324/338 |
| 4,629,986 A | 12/1986 | Clow et al. | 324/303 |
| 4,656,422 A | 4/1987 | Vail, III et al. | 324/303 |
| 4,686,364 A | 8/1987 | Herron | 250/256 |
| 4,707,658 A | 11/1987 | Frahm et al. | 324/309 |
| 4,710,713 A | 12/1987 | Taicher et al. | 324/303 |
| 4,714,881 A | 12/1987 | Givens | 324/303 |
| 4,717,876 A | 1/1988 | Masi et al. | 324/303 |
| 4,717,877 A | 1/1988 | Taicher et al. | 324/303 |
| 4,717,878 A | 1/1988 | Taicher et al. | 324/303 |
| 4,728,892 A | 3/1988 | Vinegar et al. | 324/309 |
| 4,785,245 A | 11/1988 | Lew et al. | 324/308 |
| 4,792,757 A | 12/1988 | Vail, III et al. | 324/303 |
| RE32,913 E | 4/1989 | Clark | 324/338 |
| 4,825,163 A | 4/1989 | Yabusaki et al. | 324/318 |
| 4,829,252 A | 5/1989 | Kaufman | 324/309 |
| 4,875,013 A | 10/1989 | Murakami et al. | 324/318 |
| 4,885,540 A | 12/1989 | Snoddy et al. | 324/318 |
| 4,899,112 A | 2/1990 | Clark et al. | 324/338 |
| 4,933,638 A | 6/1990 | Kenyon et al. | 324/303 |
| 4,933,640 A | 6/1990 | Kuckes | 324/339 |
| 4,949,045 A | 8/1990 | Clark et al. | 324/338 |
| 4,987,368 A | 1/1991 | Vinegar | 324/303 |
| 4,994,777 A | 2/1991 | Leupold et al. | 335/302 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,122,746 A | 6/1992 | King et al. | 324/307 |
| 5,138,263 A | 8/1992 | Towle | 324/338 |
| 5,200,699 A | 4/1993 | Baldwin et al. | 324/303 |
| 5,212,447 A | 5/1993 | Paltiel | 324/300 |
| 5,235,285 A | 8/1993 | Clark et al. | 324/342 |
| 5,280,243 A | 1/1994 | Miller | 324/303 |
| 5,291,137 A | 3/1994 | Freedman | 324/303 |
| 5,309,098 A | 5/1994 | Coates et al. | 324/303 |
| 5,349,184 A | 9/1994 | Wraight | 250/266 |
| 5,350,925 A | 9/1994 | Watson | 250/269.3 |
| 5,359,324 A | 10/1994 | Clark et al. | 340/854.3 |
| 5,363,041 A | 11/1994 | Sezginer | 324/303 |
| 5,376,884 A | 12/1994 | Sezginer | 324/303 |
| 5,379,216 A | 1/1995 | Head | 364/422 |
| 5,381,092 A | 1/1995 | Freedman | 324/303 |
| 5,387,865 A | 2/1995 | Jerosch-Herold et al. | 324/303 |
| 5,397,989 A | 3/1995 | Spraul et al. | 324/321 |
| 5,412,320 A | 5/1995 | Coates | 324/303 |
| 5,432,446 A | 7/1995 | Macinnis et al. | 324/303 |
| 5,453,692 A | 9/1995 | Takahashi et al. | 324/318 |
| 5,486,761 A | 1/1996 | Sezginer | 324/303 |
| 5,486,762 A | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,565,775 A | 10/1996 | Stallmach et al. | 324/303 |
| 5,629,623 A | 5/1997 | Sezginer et al. | 324/303 |
| 5,680,043 A | 10/1997 | Hurlimann et al. | 324/303 |
| 5,705,927 A | 1/1998 | Sezginer et al. | 324/303 |
| 5,757,186 A | 5/1998 | Taicher et al. | 324/303 |
| 5,767,674 A | 6/1998 | Griffin et al. | 324/303 |
| 5,796,252 A | 8/1998 | Kleinberg et al. | 324/303 |
| 5,869,755 A | 2/1999 | Ramamoorthy et al. | 73/152.05 |
| 5,914,598 A | 6/1999 | Sezginer et al. | 324/303 |
| 5,923,167 A | 7/1999 | Chang et al. | 324/303 |
| 5,936,405 A | 8/1999 | Prammer et al. | 324/303 |
| 5,977,768 A | 11/1999 | Sezginer et al. | 324/303 |
| 5,992,519 A | 11/1999 | Ramakrishnan et al. | 166/250.15 |
| 6,005,389 A | 12/1999 | Prammer | 324/303 |
| 6,008,646 A | 12/1999 | Griffin et al. | 324/303 |
| 6,023,163 A | 2/2000 | Flaum et al. | 324/303 |
| 6,049,205 A | 4/2000 | Taicher et al. | 324/303 |
| 6,140,817 A | 10/2000 | Flaum et al. | 324/303 |
| 6,242,912 B1 | 6/2001 | Prammer et al. | 324/303 |
| 6,246,236 B1 | 6/2001 | Poitzsch et al. | 324/303 |
| 6,316,940 B1 * | 11/2001 | Akkurt | 324/303 |
| 6,429,654 B1 * | 8/2002 | Itskovich et al. | 324/303 |

OTHER PUBLICATIONS

Carr et al., "Effects of Diffusion on Free Precision in Nuclear Magnetic Resonance Experiments," *Physical Review*, vol. 94, No. 3 (May 1, 1954), pp. 630–638.

Chandler et al., "Improved Log Quality with a Dual–Frequency Pulsed NMR Tool," *Society of Petroleum Engineers* (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Improving the Accuracy of NMR Relaxation Distribution Analysis in Clay–Rich Reservoirs and Core Samples," paper SCA 9702, in 1997 international symposium proceedings: Societyof Professional Well Log Analysts, Society of Core Analysts Chapter–at–large, p. 10, 1997.

Chen et al., "Estimation of Hydrocarbon Viscosity with Multiple TE Dual Wait–Time MRIL Logs," Society of Petroleum Engineers, SPE 49009, 1998.

Clavier et al., "Theoretical and Experimental Bases for the Dual–Water Model for interpretation of Shaly Sands," Society of Petroleum Engineers Journal, 1984, pp. 153–168.

Coates, et al., "An Investigation of a New Magnetic Resonance Imaging Log," National SPWLA Convention (Jun. 18, 1991), pp. 1–24.

Coates, et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1–15.

Coates et al., "A New Approach to Improved Log–Derived Permeability," SPWLA Fourteenth Annual Logging Symposium, May 6–9, 1973, pp. 1–27.

Coates et al., "The Magnetic Resonance Imaging Log Characterized by Comparison With Petrophysical Properties and Laboratory Core Data," Society of Petroleum Engineers, SPE 22723, 1991, pp. 627–635.

Dunn et al., "A Method for Inverting NMR Data Sets With Different Signal to Noise Ratios," SPWLA 39th Annual Logging Symposium, May 26–29, 1998.

Edwards et al., "Improved NMR Well Logs From Time–Dependent Echo Filtering," SPWLA 37th Annual Logging Symposium, Jun. 16–19, 1996.

Edwards et al., "Effects of Tool Design and Logging Speed on $T_2$ NMR Log Data," SPWLA 38th Annual Logging Symposium, Jun. 15–18, 1997.

Farrar et al., "Pulse and Fourier Transform NMR Introduction to Theory and Methods," Academic Press (1971) pp. 26–29.

Freedman et al., "Combining NMR and Density Logs for Petrophysical Analysis in Gas–Bearing Formations," SPWLA 39th Annual Logging Symposium, May 26–29, 1998.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore–Size Variations in Reservoir Sandstones," *Society of Petroleum Engineers* (1990), pp. 733–741.

Hull et al., "Field Examples of Nuclear Magnetism Logging," Journal of Petroleum Technology, 1960, pp. 14–22.

Jackson et al., "Western Gas Sands Project Los Alamos NMR Well Logging Tool Development," Los Alamos National Laboratory (Oct. 1981–Sep. 1982) pp. 1–28.

Jackson et al., "Nuclear Magnetic Resonance Well Logging," The Log Analyst, Sep.–Oct., 1984, pp. 16–30.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Kleinberg et al., "NMR Properties of Reservoir Fluids," The Log Analyst, Nov.–Dec. 1996, pp. 20–32.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Fr . . . Test of an Experimental Pulsed Nuclear Magnetism Tool," SPWLA Annual Logging Symposium (Jun. 13–16, 1993), pp. 1–23.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Nascimento et al., "Anomalous NMR Responses in Highly Permeable Sandstone Reservoirs: A Case Study," SPWLA 40th Annual Logging Symposium, May 30–Jun. 3, 1999.

Neuman et al., "Applications of Nuclear Magnetism Logging to Formation Evaluation," Journal of Petroleum Technology, vol. 34, (1982), pp. 2853–2862.

Petrakis et al., "The Utilization of Nuclear Magnetic Resonance Spectroscopy for Petroleum, Coal, Oil Shale, Petrochemicals, and Polymers, Phenomenology, Paradigms of Applications, and Instrumentation," 594 Applied Spectroscopy Reviews vol. 15 (1979) No. 2, pp. 195–260.

Prammer et al., "Theory and Operation of a New, Multi–Volume, NMR Logging System," SPWLA 40th Annual Logging Symposium, May 30–Jun. 3, 1999.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer, M.G., "NMR Pore Size Distributions and Permeability at the Well Site," *Society of Petroleum Engineers*, SPE 28368, (1994), pp. 55–64.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Setser et al., "Measurement of Remaining Oil Saturation in Northern Michigan Using Nuclear Magnetism Log Data and Pressure Core," Society of Petroleum Engineers, SPE 14276, 1985.

Singer et al., "Fast NMR Logging for Bound Fluid and Permeability," SPWLA 38th Annual Logging Symposium, Jun. 15–18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Tang et al., "LP–Zoom, a Linear Prediction Method for Local Spectral Analysis of NMR Signals," Journal of Magnetic Resonance 79, 190–196 (1988).

Waxman et al., "Electrical Conductivities in Oil–Bearing Shaly Sands," *Society of Petroleum Engineers Journal* (1968) pp. 107–122.

* cited by examiner

SYSTEM AND METHOD FOR DETERMINING OIL, WATER AND GAS SATURATIONS FOR LOW-FIELD GRADIENT NMR LOGGING TOOLS

This application is a continuation-in-part application of application Ser. No. 08/822,567 filed Mar. 19, 1997, now U.S. Pat. No. 6,242,912 which is a continuation of application Ser. No. 08/542,340, filed Oct. 12, 1995, abandoned, which applications are hereby incorporated by reference.

BACKGROUND OF THE INVENTION

The present invention relates to nuclear magnetic resonance (NMR) logging and is directed more specifically to a system and method for detecting the presence and estimating the quantity of gaseous and liquid hydrocarbons in the near wellbore zone.

Petrophysical parameters of a geologic formation which are typically used to determine whether the formation will produce viable amounts of hydrocarbons include the formation porosity PHI, fluid saturation S, the volume of the formation, and its permeability K. Formation porosity is the pore volume per unit volume of formation; it is the fraction of the total volume of a sample that is occupied by pores or voids. The saturation S of a formation is the fraction of a its pore volume occupied by the fluid of interest. Thus, water saturation $S_W$ is the fraction of the pore volume which contains water. The water saturation of a formation can vary from 100% to a small value which cannot be displaced by oil, and is referred to as irreducible water saturation $S_{Wirr}$. For practical purposes it can be assumed that the oil or hydrocarbon saturation of the formation $S_O$ is equal to $S_O=1-S_W$. Obviously, if the formation's pore space is completely filled with water, that is if $S_W=1$, such a formation is of no interest for the purposes of an oil search. On the other hand, if the formation is at $S_{Wirr}$ it will produce all hydrocarbons and no water. Finally, the permeability K of a formation is a measure of the ease with which fluids can flow through the formation, i.e., its producibility.

Nuclear magnetic resonance (NMR) logging is among the most important methods which have been developed to determine these and other parameters of interest for a geologic formation and clearly has the potential to become the measurement of choice for determining formation porosity. At least in part this is due to the fact that unlike nuclear porosity logs, the NMR measurement is environmentally safe and is unaffected by variations in matrix mineralogy. The NMR logging method is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the so called spin-spin relaxation time constant $T_2$ (also known as transverse relaxation time) which is an expression of the relaxation due to non-homogeneities in the local magnetic field over the sensing volume of the logging tool.

Another measurement parameter used in NMR well logging is the formation diffusion D. Generally, diffusion refers to the motion of atoms in a gaseous or liquid state due to their thermal energy. The diffusion parameter D is dependent on the pore sizes of the formation and offers much promise as a separate permeability indicator. In an uniform magnetic field, diffusion has little effect on the decay rate of the measured NMR echoes. In a gradient magnetic field, however, diffusion causes atoms to move from their original positions to new ones, which moves also cause these atoms to acquire a different phase shifts compared to atoms that did not move, and will thus contribute to a faster rate of relaxation. Therefore, in a gradient magnetic field diffusion is a logging parameter which can provide independent information about the structure of the geologic formation of interest, the properties of the fluids in it, and their interaction.

It has been observed that the mechanisms which determine the values of $T_1$, $T_2$ and D depend on the molecular dynamics of the sample being tested. In bulk volume liquids, typically found in large pores of the formation, molecular dynamics is a function of molecular size and inter-molecular interactions which are different for each fluid. Thus, water, gas and different types of oil each have different $T_1$, $T_2$ and D values. On the other hand, molecular dynamics in a heterogeneous media, such as a porous solid which contains liquid in its pores, differs significantly from the dynamics of the bulk liquid and generally depends on the mechanism of interaction between the liquid and the pores of the solid media. It will thus be appreciated that a correct interpretation of the measurement parameters $T_1$, $T_2$ and D can provide valuable information relating to the types of fluids involved, the structure of the formation and other well logging parameters of interest.

On the basis of the $T_2$ spectra, two specific methods for gas measurements are known in the prior art and will be considered briefly next to provide relevant background information. The first method is entitled "differential spectrum method" (DSM). The DSM is based on the observation that often light oil and natural gas exhibit distinctly separated $T_2$ measurements in the presence of a magnetic field gradient, even though they may have overlapping $T_1$ measurement values. Also, it has been observed that brine and water have distinctly different $T_1$ measurements, even though their $D_0$ values may overlap. The DSM makes use of these observations and is illustrated in FIG. 1 in a specific example for a sandstone reservoir containing brine, light oil and gas.

A second method known in the art is called "shifted spectrum method" (SSM). The SSM is illustrated in FIGS. 2A–B. Specifically, FIG. 2A shows synthetic $T_2$ decay curves in a gas bearing zone. The solid curve is for the short interecho time (≈0.6 msec) and the dashed curve corresponds to a longer interecho time of about 2.4 msec. FIG. 2B illustrates the $T_2$ spectra obtained from the inversion of the synthetic echo trains in FIG. 2A. The solid spectrum corresponds to the shorter interecho time, while the dashed spectrum line corresponds to the longer interecho time. In FIG. 2B the solid spectrum line corresponds to both brine and gas. The signal from gas is shifted out of the detectability range, so that the single spectrum peak is due to brine.

While prior art DSM and SSM methods provide a possible working approach to detection of gas using solely NMR data, the methods also have serious disadvantages which diminish their utility in practical applications. Specifically, typically two separate logging passes are required and therefore the methods show relatively poor depth matching properties on repeat runs. Furthermore, subtraction of signals from different logging passes is done in the $T_2$ spectrum domain which may result in losing valuable information in the transformation process, especially when the received signals have low signal-to-noise ratios (SNRs). In fact, for a typical logging pass, low hydrocarbon index (HI) of the gases in the formation, and relatively long $T_1$ times generally lead to low SNR of the received signals. After transformation into the $T_2$ spectrum domain even more information can be lost, thus reducing the accuracy of the desired parameter estimates.

In the parent application Ser. No. 08/822,567 filed Mar. 19, 1997, which is incorporated herein by reference for all purposes, a well logging system and method are disclosed for detecting the presence and estimating the quantity of gaseous and liquid hydrocarbons in the near wellbore zone. The approach presented in this application effectively addresses some of the concerns associated with prior art DSM and SSM methods. In particular, the proposed system uses a gradient-based, multiple-frequency NMR logging tool to extract signal components characteristic for each type of hydrocarbons. To this end, a data acquisition method is proposed in which measurements at different frequencies are interleaved to obtain, in a single logging pass, multiple data streams corresponding to different recovery times and/or diffusivity for the same spot in the formation. The resultant data streams are processed to determine mineralogy-independent water and hydrocarbon saturations and porosity estimates. Gas and oil saturations are used to obtain accurate estimates of the water content, permeability and other parameters of interest.

In most practical applications the approach used in the parent application is completely adequate and has been demonstrated to work. However, this approach relies on the presence of a static field gradient of typically 10–20 gauss/cm, and may not work well in an emerging class of wireline and LWD NMR logging tools that use lower field strengths, different field patterns and deeper depths of investigations (DOI).

Lower field gradients are important in achieving large sensitive volumes and the sensitivity required to perform deeper reading measurements. The combination of a lower field strength and deeper DOI's results in dramatically reduced static field gradients on the order of 0.3–3 gauss/cm. For the measurement method disclosed in the parent application, which employs variable wait times (1 sec to 12 sec) and fixed echo spacings (typ. 1 msec), it will generally be difficult to differentiate between the oil, water and gas phases in a weak gradient, because the method relies on differences in apparent $T_2$ decay rates due to diffusion in a gradient field. One possible solution is to increase the echo spacing (i.e., from 1 msec to 10 msec), but such an approach would result in a significant loss of sensitivity because the sampling rate is only one-tenth of its original value. Therefore, it will be apparent that low-gradient logging tools require modified methods for successful gas/oil detection and quantification.

SUMMARY OF THE INVENTION

In accordance with a preferred embodiment of the present invention a novel system and method are disclosed for the interpretation of NMR measurements of $T_1$, D and effective $T_2$ parameters made with a NMR logging tool using low field gradient magnetic fields. The present invention is based on a multi-frequency, gradient based logging tool providing the capability of conducting substantially simultaneous NMR measurements in adjacent non-overlapping resonant volumes of the geologic formation of interest. In particular, by hopping the resonant frequency of the device and thus sensing non-overlapping volumes of the formation, in accordance with a preferred embodiment of the present invention the time between experiments is reduced substantially without compromising the $T_1$ relaxations or adopting imprecise $T_1/T_2$ empirical relationships.

In one aspect, the present invention uses the multi-frequency capabilities of an NMR tool along with a data acquisition method suitable for the detection of gas on the basis of at least two sets of data points corresponding to a long ($T_{RL}$) and short ($T_{RS}$) recovery times, respectively. To this end, an interleaved pulse sequence is proposed in which at least two CPMG pulses associated with a first resonant frequency are followed by at least two CPMG pulses associated with a second resonant frequency. Due to the fact that each resonant frequency excites protons in a separate volume of the formation, pairs of complex data points can be collected at substantially the same depth mark, such that the first data point corresponds to a short recovery time $T_{RS}$ while the second data point corresponds to a long recovery time $T_{RL}$.

In accordance with a preferred embodiment of the present invention, the sequence of data pairs is used next to form two complex time-domain signal vectors x and y corresponding to the long and the short recovery times, respectively. Following calibration, a difference and a sum signal vectors (x−y) and (x+y) are formed. The difference signal is phase corrected to obtain a real-time signal using phase information from the sum signal. Next, matched filters corresponding to a gas phase and an oil phase are computed, in real time, using information about reservoir temperature, pressure and other known probe and/or formation properties. The phase-corrected difference signal is then filtered using the matched filters to separate oil and gas signal components from the input NMR signals. The output signals from the matched filters are next used to obtain gas- and oil-porosity estimates and further to reconstruct the oil and gas components in the original measurement signals. The reconstructed components are subtracted from the sum signal 1/2(x+y) to provide only the brine component of the original signal. This brine component is finally subjected to $T_2$ inversion to obtain an estimate of the irreducible water saturation and water porosity. To further increase the separation between different hydrocarbon phases in the formation, diffusion-weighted measurements can also be used according to the SSM approach.

The system and method in accordance with the present invention have been shown to be very sensitive due to the fact that the gas and oil components of the original signal are determined from the original signals, prior to $T_2$ spectrum inversion. The method of the present invention has been demonstrated to give more accurate parameter estimates than other presently available NMR logging techniques and can be used advantageously in low-porosity formations, where low signal-to-noise ratios (SNRs) tend to broaden all $T_2$ components. Additionally, corrections for hydrogen index (HI) and incomplete longitudinal recovery are also provided to calculate estimates of gas-filled porosity and to correct both apparent NMR porosity (MPHI) and free fluid index FFI, which are necessary to obtain accurate estimates of formation permeability.

In another aspect, the present invention is based on the use of a modified CPMG (Carr-Purcell-Meiboom-Gill) sequence that is characterized by two echo spacings. The first echo is subject to a variable echo spacing TD; ranging from approximately 1 ms to hundreds of milliseconds. With such a large possible range for the echo spacing TD, the diffusion characteristics of the fluid(s) involved can be made a dominant factor for amplitude decay. In a preferred embodiment, the second and all following echoes are generated with short spacings (TE, typically 1 msec). In this period, the influence of diffusion is negligible in a low field gradient, and a dense sampling regime is maintained, resulting in good sensitivity. The amount of amplitude loss incurred in the TD interval is directly related to the diffusivity of the hydrogen-bearing fluids. In a preferred embodiment, TD is a parameter that varies from a low of TE (i.e., the case in which the modified sequence reduces to a simple CPMG sequence) to highs of hundreds of milliseconds.

BRIEF DESCRIPTION OF THE DRAWINGS

The invention will be described next in detail by reference to the following drawings in which:

FIG. 12A illustrates the case in which the modified sequence reduces to a CPMG pulse sequence with a single echo spacing. FIGS. 12B and 12C illustrate pulse sequences with increased diffusion time TD.

FIG. 15A shows an implementation of the method of the present invention using a modified TD/TE pulse sequence for two frequencies (i.e., two sensitive volumes). FIG. 15B illustrates the use of the modified pulse sequence in the case of four operating frequencies (sensitive volumes).

DETAILED DESCRIPTION OF THE PREFERRED EMBODIMENTS

During the course of the description like numbers will be used to identify like elements shown in the figures. Bold face letters represent vectors, while vector elements and scalar coefficients are shown in standard print.

Equipment

In order to separate signal contributions from different fluids, an NMR tool must be able to operate in a three-dimensional parameter space: $T_2$ (transverse decay time), measured by a CPMG pulse-echo sequence: $T_1$ (longitudinal polarization time), measured by variable saturation-recovery times; and D (apparent, restricted diffusivity), measured by varying the CPMG pulse-echo spacing τ in the presence of a magnetic field gradient.

Figure 1:
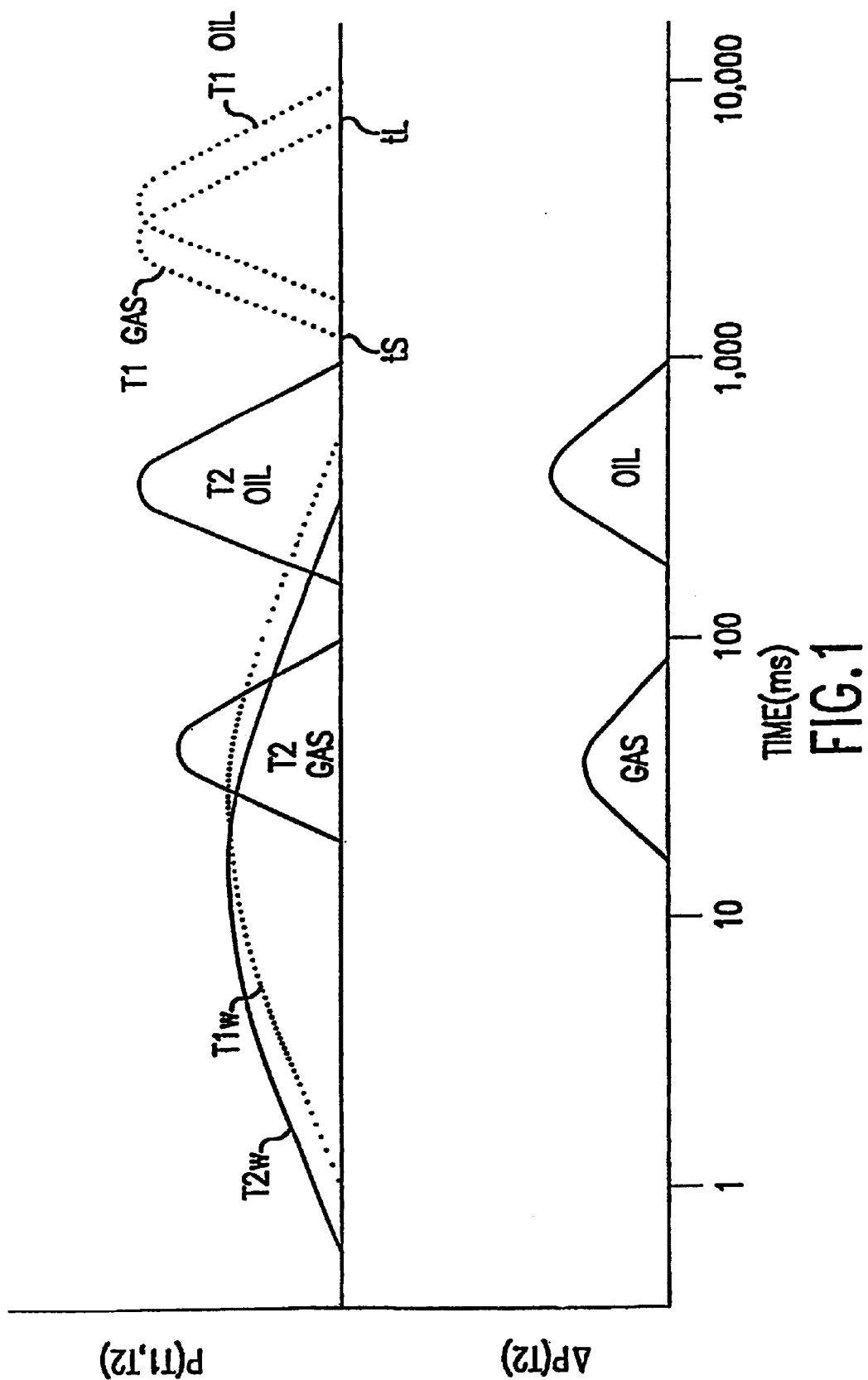
FIG. 1 is an illustration of the differential spectrum method for identifying the presence of gaseous components.
Figure 2A:
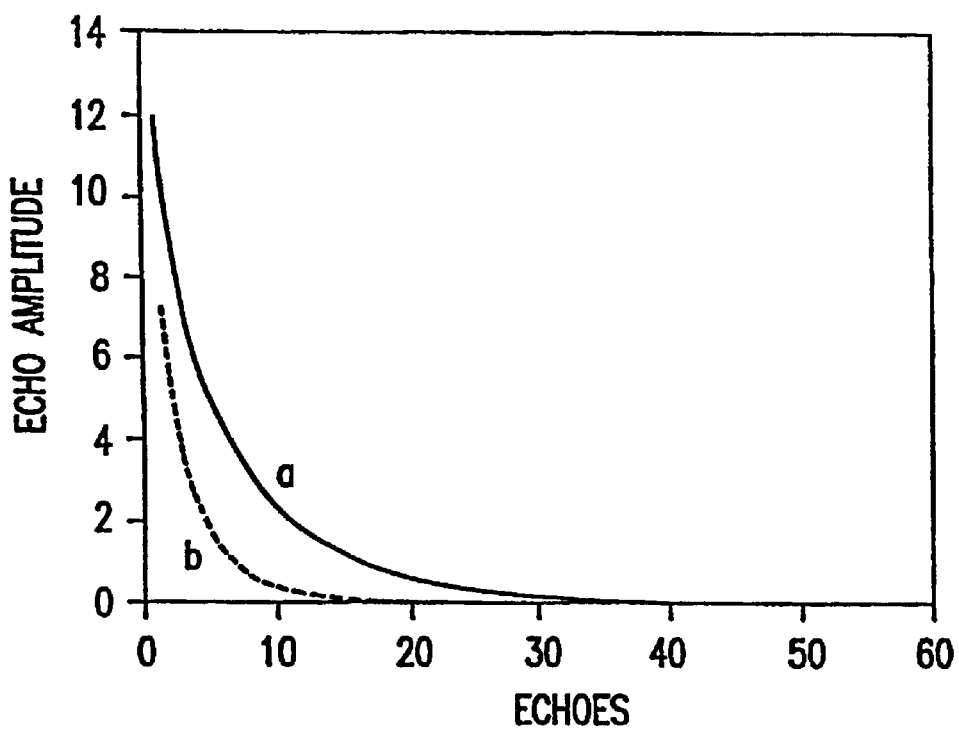
FIG. 2A illustrates synthetic $T_2$ decay curves used in the Shifted Spectrum method.
Figure 2B:
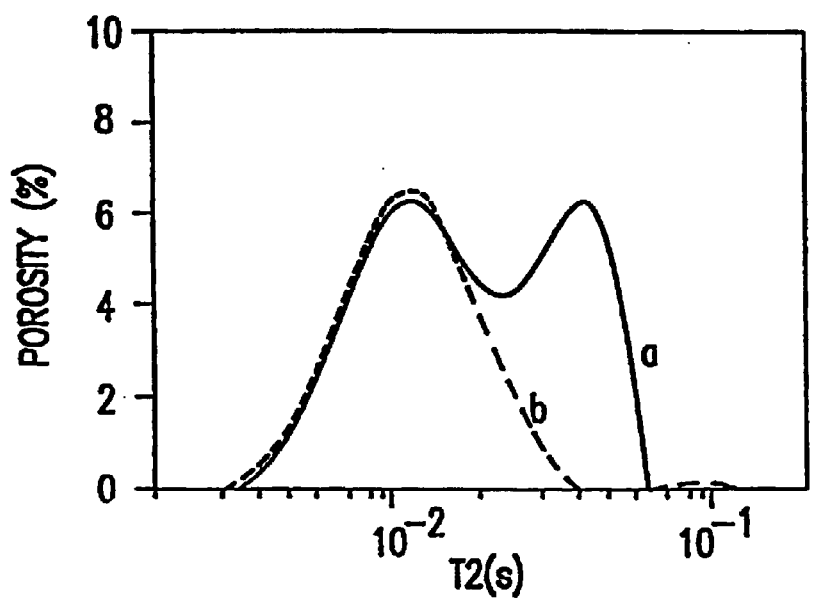
FIG. 2B shows $T_2$ spectra obtained from inversion of the synthetic echo trains in FIG. 2A.
Figure 3A:
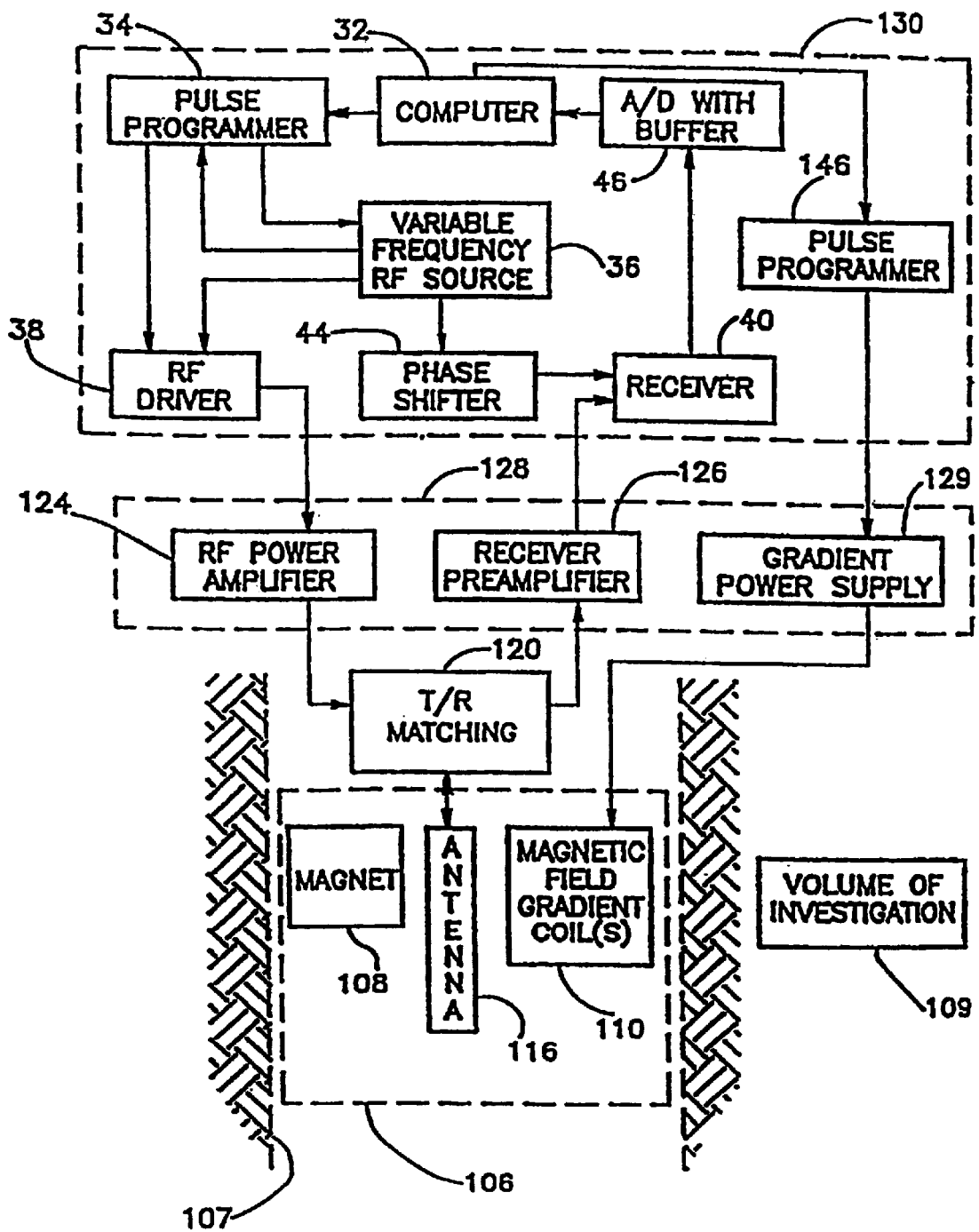
FIG. 3A shows a specific embodiment of the gradient-based logging tool of the present invention.

In a preferred embodiment of the present invention these measurements in a moving logging tool are enabled using the system illustrated schematically in FIGS. 3(A–C). In particular, FIG. 3A illustrates, in relatively general form, apparatus for carrying out NMR borehole diffusion coefficient determinations in accordance with a preferred embodiment of the present invention. The apparatus includes a first portion 106, which is arranged to be lowered into a borehole 107 in order to examine the nature of materials in the vicinity of the borehole.

The first portion 106 comprises a magnet or a plurality of magnets 108 which generate a substantially uniform static magnetic field in a volume of investigation 109. The first portion 106 also comprises an RF antenna coil 116 which produces an RF magnetic field at the volume of investigation 109 which field is substantially perpendicular to the static magnetic field.

In addition to the static magnetic field gradient generated by magnet(s) 108, an optional magnetic field gradient coil, or plurality of coils, 110 can also be used to generate a magnetic field gradient at the volume of investigation 109. This additional contribution to the magnetic field has a field direction preferably collinear with the substantially uniform field and has a substantially uniform magnetic field gradient, which may or may not be switched on and off by switching the dc current flowing through the coil or coils 110. The magnet or magnets 108, antenna 116 and the gradient coil 110 constituting portion 106 are also referred to as a probe.

The antenna together with a transmitter/receiver (T/R) matching circuit 120 typically include a resonance capacitor, a T/R switch and both to-transmitter and to-receiver matching circuitry and are coupled to an RF power amplifier 124 and a receiver preamplifier 126. A power supply 129 provides the dc current required for the magnetic field gradient generating coils 110. All the elements described above are normally contained in a housing 128 which is passed through the borehole. Alternatively, some of the above elements may be located above ground.

Indicated as block 130 is control circuitry for the logging apparatus including a computer 32, which provides a control output to a pulse programmer 146 which receives an RF input from a variable frequency RF source 36. Pulse programmer 146 controls the operation of the variable frequency RF source 36 as well as an RF driver 38, which receives an input from variable frequency RF source 36 and outputs to RF power amplifier 124.

The complex time-domain signal from the RF receiver preamplifier 126 is supplied to an RF receiver 40 which optionally receives input from a phase shifter 44. Phase shifter 44 receives an input from variable frequency RF source 36. As discussed in more detail next, in a preferred embodiment of the present invention phase correction is done using signal processing algorithms instead. Receiver 40 outputs via an A/D converter with a buffer 46 to computer 50 for providing desired well logging output data for further use and analysis. Pulse programmer 146 controls the gradient coil power supply 129 enabling and disabling the flow of current, and hence the generation of static or pulsed field gradients, according to the commands of the computer 50. Some or all of the elements described hereinabove as being disposed in an above-ground housing, may instead be disposed below ground. Improved devices and measurement methods which can be used for the probe 106 are described generally in U.S. Pat. Nos. 4,710,713; 4,717,876; 4,717,877; 4,717,878, 5,212,447; 5,280,243; 5,309,098 and 5,412,320 all of which are commonly owned by the assignee of the present invention. A specific embodiment of the tool which can be used in accordance with the present invention is also discussed in detail in Chandler et al., "Improved Log Quality with a Dual-Frequency Pulsed NMR Tool," paper SPE 28365, presented at the 69-th Annual Technical Conference and Exhibition, Society of Petroleum Engineers, New Orleans, Sep. 25–28, 1994. The contents of these patents and the Chandler et al. paper are hereby expressly incorporated for all purposes.

Figure 3B:
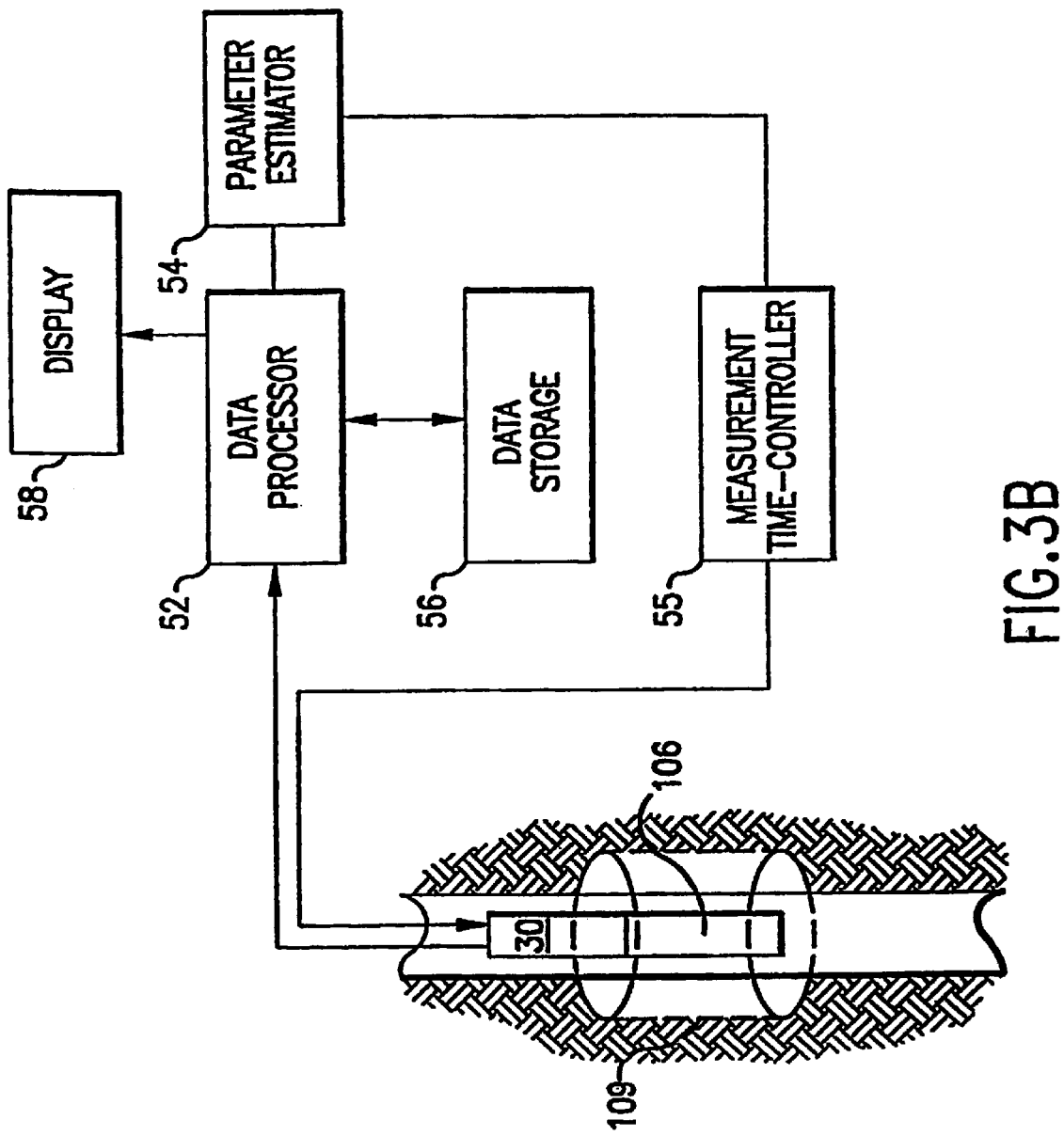
FIG. 3B is a block diagram of the system in accordance with a specific embodiment of the present invention which shows individual block components for controlling data collection, processing the collected data and displaying the measurement results.

FIG. 3B is a block diagram of the system in accordance with a specific embodiment of the present invention which shows individual block components for controlling data collection, processing of the collected data and displaying the measurement results. In FIG. 3B the MRI electronics 30 comprises an MRI probe controller and pulse echo detection electronics. The output signal from the detection electronics is processed by data processor 52 to analyze the relaxation characteristics of the sample. The output of the data processor 52 which in accordance with a preferred embodiment of the present invention comprises at least two complex time-domain data sets is provided to the parameter estimator 54. Measurement cycle controller 55 provides an appropriate control signal to the MRI probe. The processed data from the log measurement is stored in data storage 56. Data processor 52 is connected to display 58 which is capable of providing a graphical display of one or more measurement parameters, preferably superimposed on display data from data storage 56. The components of the system of the present invention shown in FIG. 3B can be implemented in hardware or software, or any combination thereof suitable for practical purposes.

As indicated above, the MRIL tool used in a preferred embodiment of the present invention is digitally based, so that raw echo data is digitized at the carrier frequency and all subsequent filtering and detection is performed in the digital domain. For the purposes of the present invention, the critical feature of the tool is its ability to operate at different frequencies.

Figure 3C:
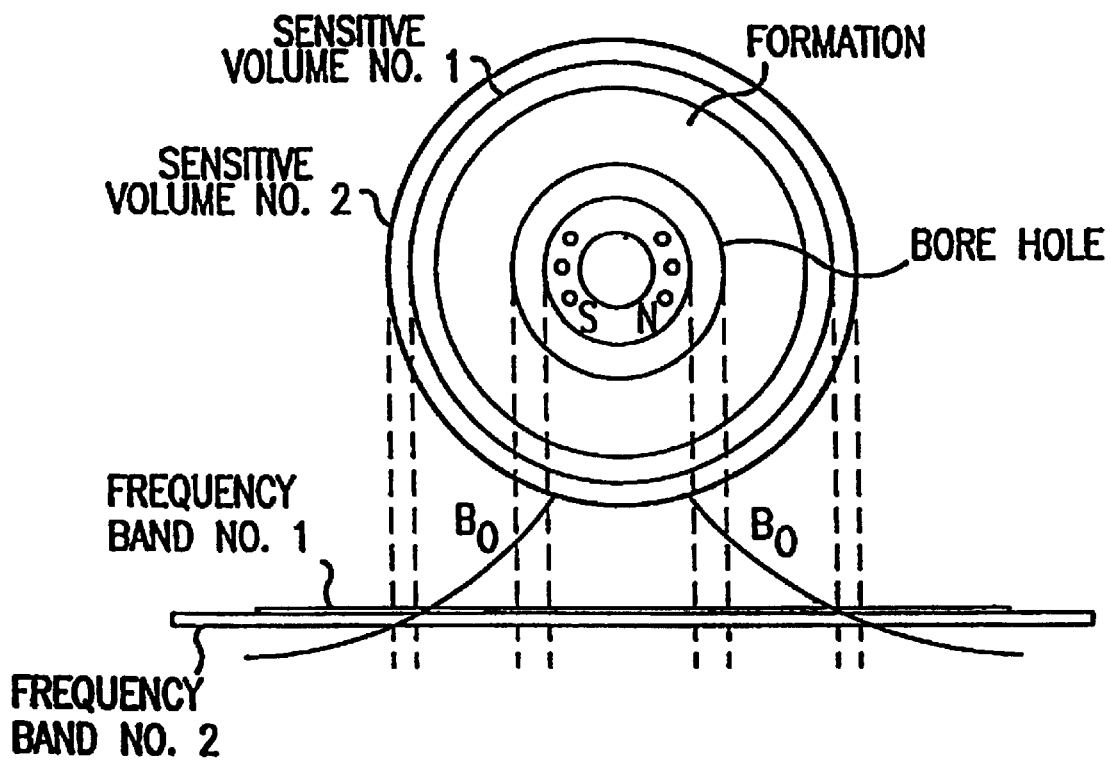
FIG. 3C illustrates the operation of a gradient logging tool in a multi-frequency mode at the example of dual-volume investigation.

Specifically, in a preferred embodiment the system of the present is capable of "hopping" from one operating frequency to another, the effect of which is to shift the radial position of the resonant volume for the tool. The frequency shift is selected in such manner that at least two non-overlapping resonant volumes are formed; each new resonant volume associated with a different frequency being filled with fully relaxed protons. Hopping between two or more (i.e., K) frequencies thus allows reducing the time between experiments approximately by a factor of K, without compromising complete $T_1$ measurements or adopting imprecise empirical $T_1/T_2$ relationships; the logging speed for the tool can accordingly be increased approximately K times. This feature is illustrated in FIG. 3C in which hopping between two different frequencies is shown to result in conducting measurements in two non-overlapping resonant volumes. In the specific example illustrated in FIG. 3C each frequency band is about 6 kHz wide and the two mean band frequencies are offset by about 15 kHz. This mode of operation forms two concentric annuli, each 0.04 inch (0.1 cm) thick, separated center to center by about 0.09 inches (0.23 cm).

The logging speed of the device used in a preferred embodiment of the present invention depends upon different factors including the SNR of the received signal, the desired log precision and vertical resolution, and the cycle time permitted by the $T_1$ parameter of the formation. Preferably, for greater than 95% recovery within a single resonant volume, the recovery time should satisfy the requirement $T_R \leq 3T_1$. As a consequence of the multi-frequency operation, the cycle time is only slightly longer than the $T_R$ normalized to the number of frequencies employed. (i.e. $T_C \approx T_R/2$ for two operating frequencies).

Figure 4:
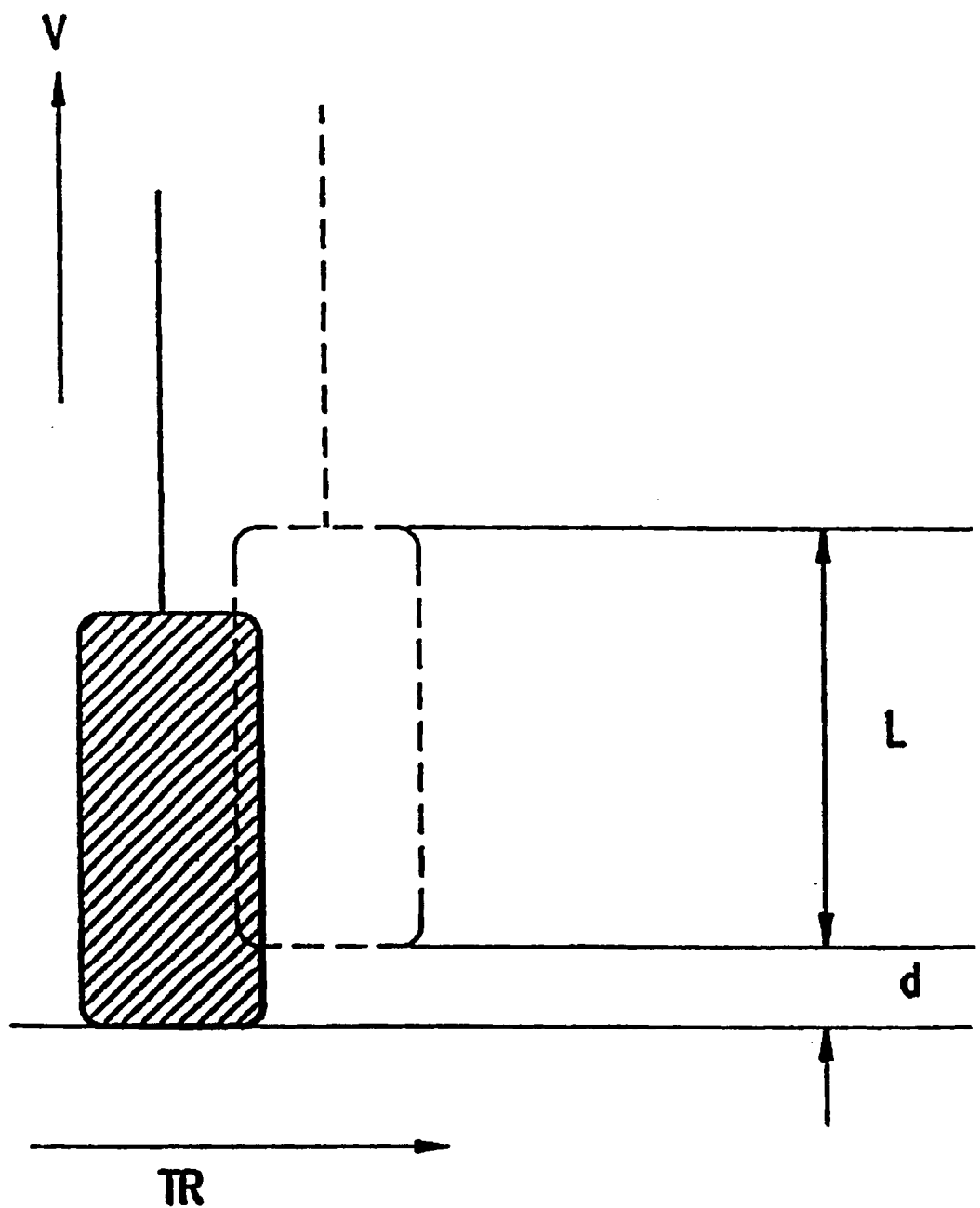
FIG. 4 is a schematic illustration of the connection between saturation-recovery time interval TR, logging speed v and aperture length L.

The MRIL tool used in a preferred embodiment of the present invention generally has a vertical excitation/response function that can be represented by a near-perfect rectangular aperture. In a specific embodiment, a high vertical resolution, 24" (60.96 cm) long aperture, or a lower vertical resolution, 43" (109.22 cm) long, aperture are used. In order to perform $T_1$-weighted signal measurements, as discussed in detail below, it is required that the formation volume being sensed remains substantially unchanged over the course of a recovery period. Specifically, for a moving tool, it has been determined that volume changes of about 10–20% still provide adequate measurement accuracy. This condition is illustrated in FIG. 4 which shows the relationships between saturation-recovery time interval $T_R$, logging speed v and aperture length L. Using the notations in FIG. 4, it is possible to impose either a minimum aperture length or a maximum tool logging speed requirement which must satisfy the condition for substantial measurement stationarity. For example, in the specific embodiment of a 24" long aperture, assuming recovery time $T_R$=2 s, and imposing a 10% accuracy requirement, it can be seen that the maximum allowed tool speed is v=5*2.4"/2 s=6 ft/min (3.05 cm/sec).

For the alternate configuration using a 43" long antenna, under the same assumptions the maximum tool speed is about 11 ft/min (5.588 cm/sec).

In accordance with the present invention, for the purposes of making $T_1$ weighted measurements with a moving logging tool at least one long saturation-recovery (SR) interval is required, preferably of about 8–10 sec. It should be noted that for such an interval logging data is substantially insensitive to vertical tool displacement because at the end of the interval the formation magnetization is already close to an equilibrium. The transverse magnetization left after a CPMG sequence is quickly dephased in the strong gradient field. At this point, a saturation-recovery (SR) measurement can be started, as known in the art. The recovered magnetization is read out by the next CPMG train.

In addition to the relatively long SR interval, one or more measurements are made in accordance with a preferred embodiment of the present invention using shorter recovery intervals, as described in more detail next.

Random lateral tool motion is a source of concern for the validity of the downhole $T_1$-weighted measurements in accordance with the present invention. The reason is that since the sensitive volume for the tool resembles a cylindrical slice of about 1–2 mm thickness, lateral swaying of the tool could cause an influx of fully polarized magnetization and thus give incorrect measurements. Studies of actual log data repeatedly acquired over the same zones, however, show monotonic recovery behavior of sequences with increasing SR intervals, indicating that lateral tool motion generally has a negligible effect on the actual measurements. Further evidence that side effects due to lateral motion of the tool are insignificant is provided by the consistency of MPHI and FFI measurements made with the tool, which are both independent of the $T_1$ parameter.

Another source of concern in NMR logging is the relatively shallow depth-of-investigation which, due to the generally cylindrical shape of the resonance volume of the tool, also depends on the borehole size. Thus, in some cases shallow depth-of-investigation along with the fact that invading fluid in the borehole replaces gas can lead to a reduction in the gas effect which can be sensed by the tool. It should be noted, however, that the MRIL tool's sensitive volume has an approximately 4" (10.16 cm) blind zone extending from the borehole wall. The presence of such blind zone effectively limits the influence of fluid invasion. Experimentally, in most cases residual hydrocarbon saturations seen by the tool have been shown to be sufficient for hydrocarbon detection purposes and can be close to uninvaded saturations.

The CPMG pulse sequences used with the MRIL tool in accordance with the present invention have been described generally in U.S. Pat. No. 5,212,447 assigned to the assignee of the present application. Also discussed in this patent are specific methods of conducting NMR measurements, including derivations of the diffusion coefficient D and/or $T_2$. The relevant portions of the disclosure of the U.S. Pat. No. 5,212,447 are expressly incorporated herein for all purposes. The MRIL tool used in accordance with a preferred embodiment of the present invention stores multiple pulse sequences downhole, in a memory (not shown in FIGS. 3A and B) within probe 106. These sequences are then activated by commands from the measurement time controller 55 of the surface system. At the surface, raw tool data are separated into data streams and associated with the correct calibration and correction tables in data processor 52. An essentially unlimited number of pulse sequences can be used quasi-simultaneously, as described in more detail next. In an alternative preferred embodiment of the present invention the operation of the tool can be re-programmed on command from surface controller 55.

In accordance with another aspect of the invention, LWD NMR logging tools are desirable that use lower field strengths, different field patterns and deeper depths of investigations (DOI). An example of such a tool is disclosed in European Patent Application 99200567.8 (Document EP 0 940 688 A2) entitled "NMR logging-while drilling tool generating an axisymmetric magnetic field having straight contour lines in the resonance region." Another example is provided by the basic magnet configuration described in U.S. Pat. No. 4,629,986. The above references are incorporated herein by reference for all purposes.

Signal Modeling and Corrections

In accordance with a preferred embodiment of the present invention several parameters which correspond to the gas and the oil phases of the formation are computed in real time. Due to the fact that logging conditions dynamically change during the course of a pass, correction for various factors which may affect the accuracy of the measurements have to be made. In the following paragraphs, a brief discussion is presented on the specifics of the parameter computations and the required corrections used in accordance with a preferred embodiment of the present invention to estimate the relative quantities of gas and oil in a formation of interest.

1) Corrections for the Influence of $T_1$ on Diffusion Measurements

It is known in the art that the static field gradient required for downhole diffusion measurements induces stimulated echo effects within a CPMG echo train. These stimulated echoes partially undergo $T_1$ relaxation and therefore benefit less from the re-focusing effects of repeated $\pi$ pulses in a standard CPMG sequence. In accordance with a preferred embodiment of the present invention this problem can be treated by introducing the concept of "effective" relaxation times, as described in more detail next.

In particular, it is known that the classic Carr-Purcell expression for spin echo attenuation due to transverse relaxation and diffusion in a field gradient which, using the standard notations above, is given by the expression:

$$M_{xy}(t) = M_0 \exp\left(\left(-\frac{t}{T_2}\right) + \left(\frac{1}{3}\gamma^2 G^2 \tau^2 Dt\right)\right) \quad (1)$$

strictly speaking is valid only if: (a) the gradient G is small, or (b) if only the on-resonance portion of the spin spectrum is utilized. As indicated above, however, the MRIL tool operates with a relatively strong gradient field, on the order of about 15–25 G/cm. In addition, low signal-to-noise considerations make it necessary to utilize the full bandwidth of the tool, so that strong off-resonance effects are necessarily included in the echo signals. Thus, for example, even for the simplest $T_2/D$ experiment which requires at least two different pulse-echo spacings $\tau$ a correction in the expression in Eq. (1) is required in order to avoid systematic errors. Consequently, the observed echo decay signal has to be modeled as a complex superposition of longitudinal relaxation, transverse relaxation and different diffusion times.

Therefore, in accordance with the present invention, the signal observed at the N-th echo is modeled as a superposition of all possible combinations of transitions between transverse and longitudinal magnetization and is given by the expression:

$$M_{xy}(2\tau N) = M_0 \sum_{i=1}^{N} A_i \exp\left(-\frac{2\tau}{T_1}(N-i) - \frac{2\tau}{T_2}i - 2\left(N-\frac{2i}{3}\right)\gamma^2 G^2 \tau^3 D\right) \quad (2)$$

Using the expression in Eq. (2), the effect of diffusion dephasing is taken into account by introducing "effective" transverse relaxation times $T_1^\dagger$ and $T_2^\dagger$ given by the following expressions:

$$1/T_1^\dagger = 1/T_1 + \gamma^2 G^2 \tau^2 D$$

$$1/T_2^\dagger = 1/T_2 + 1/3 * \gamma^2 G^2 \tau^2 D \quad (3)$$

It can be shown that direct echoes (i=N) decay with a rate $1/T_2^\dagger$; indirect echo decay (i<N) is controlled by $1/T_1^\dagger$ and by $1/T_2^\dagger$. Without diffusion, indirect echoes decay either slower or at the same rate as direct echoes. With very fast diffusion, however, indirect echoes drop out faster than direct ones. The effect on combined echo amplitudes primarily depends on the receiver's bandwidth and has been determined to require an about 15% correction at high diffusion rates.

It should be noted that the expressions for the effective relaxation rates in Eq. (3) refer to the echo decay process, and not to the recovery of longitudinal magnetization, which is controlled by $T_1$. For gases, both effective relaxation times are dominated by the diffusion term in a gradient field and therefore $T_1 \gg T_1^\dagger \approx T_2^\dagger/3$. In this case, the echo train decays slightly faster than expected, and an analysis based on the standard Carr-Purcell formula will overestimate the diffusion parameter D. This problem is corrected by inserting into the Carr-Purcell formula of an effective pulse-echo spacing $\tau_{\mathit{eff}}$, which incorporates the influence of both pulse width and receiver bandwidth:

$$1/T_2^\dagger = 1/3 * (\tau_{\mathit{eff}} \gamma G)^2 D \quad (4)$$

It has been determined that for the MRIL systems used in accordance with a preferred embodiment of the present invention, the ratio $\tau_{\mathit{eff}}/\tau = 1.08$, thus resulting in a 16% correction for calculated gas diffusivities.

2) Magnetic Field Gradient and Probe Temperature

As evident from Eq. (4), the prediction of $T_2^\dagger$ in the gas phase generally requires knowledge of the field gradient G, which is dependent on the probe temperature. A specific example of measurements of the depth-of-investigation (diameter of the sensitive zone) and the magnetic field gradient values, as functions of probe temperature, are summarized in Table 1.

TABLE 1

Sensitive diameter and magnetic field gradient of an MRIL ®/C 6" tool as functions of probe temperature.

| Temperature | Diameter | Field Gradient |
|---|---|---|
| 25° C. | 40.6 cm | 16.6 G/cm |
| 50° C. | 39.7 cm | 17.0 C/cm |
| 75° C. | 38.9 cm | 17.4 G/cm |
| 100° C. | 37.8 cm | 17.9 G/cm |
| 125° C. | 36.8 cm | 18.4 G/cm |
| 150° C. | 35.8 cm | 18.9 G/cm |

Typical values used in Eq. (4) are $\tau_{\mathit{eff}} = 0.65$ ms, $\tau = 26750$ s$^{-1}$G$^{-1}$, and G=18 G/cm. Probe temperature, as reported by a sensor embedded in the permanent magnet of the MRIL tool, is always recorded, which allows the calculation of the field gradient G at any point on the log.

3) Parameterization of HI, $T_1$ and $T_2$

The matched filter signal processing method of the present invention, described in more detail below, requires the calculation of hydrocarbon (oil and gas) signatures. These components are assumed to be the non-wetting phase, i.e., to be generally characterized by their bulk relaxation properties. As known in the art, the effects of temperature and pressure on $T_1$ and D of the gas phase substantially cancel each other, resulting in fairly stable and predictable values for both parameters, for which mathematical expressions are available. On the other hand, the corresponding values for the oil phase are generally dependent on the formation and are determined in accordance with the present invention from sample measurements conducted prior to the logging experiment.

Figure 5A:
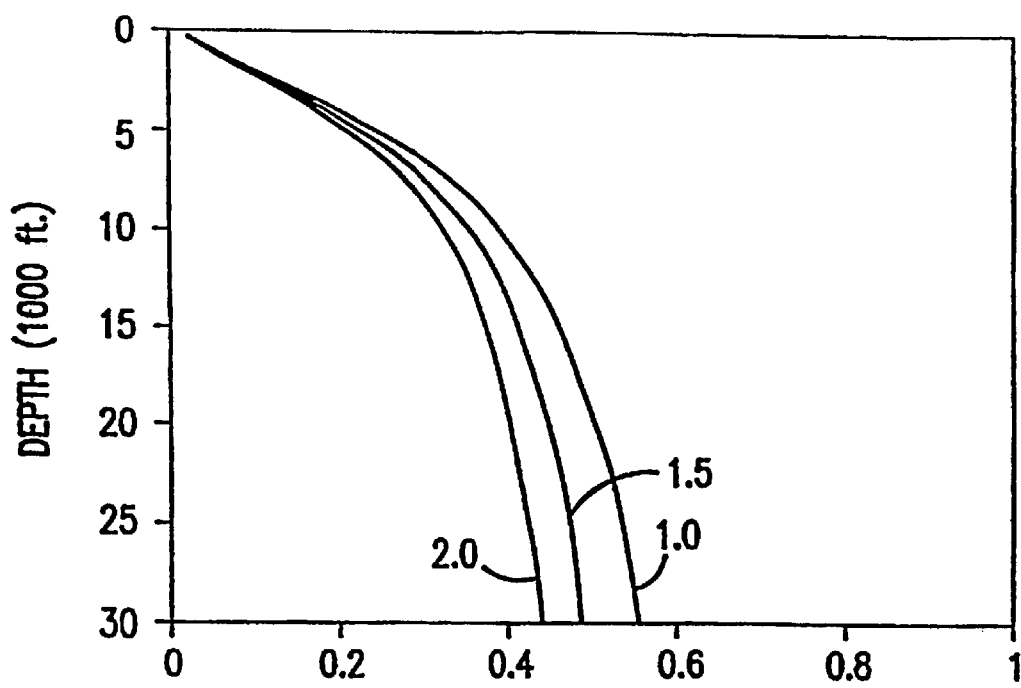
FIG. 5A shows the hydrogen index (HI) of methane as a function of depth at temperature gradients of 1, 1.5 and 2° F./100 ft.

In particular, the hydrogen index (HI) of oil is assumed to be 1.0. The measured drop in NMR porosity is typically observed in gas zones, because $HI_g < 1$. Most natural gases are predominantly methane. FIG. 5A shows $HI_g$ variations between about 0.2 and 06 for a methane gas under typical conditions. In overpressured reservoirs $HI_g$ can be about 0.7. Accordingly, the gas HI is sufficient to give readily detectable signals from gas. For methane gas, in accordance with a preferred embodiment of the present invention the corresponding index $HI_g$ is estimated mathematically using the expression 2.25×$\rho$, where $\rho$ is the gas density in g/cm$^3$, calculated by solving the equation of state. For gases other than methane, or for mixed gases, the multiplying factor is less than 2.25. For example, for a typical gas mix, characterized as $C_{1.1}H_{4.2}$, the factor becomes 2.17. In an alternative preferred embodiment of the present invention, the hydrogen index of different hydrocarbons can also be estimated using the expressions presented, for example, in "Schlumberger: Log Interpretation Principles/Applications," Schlumberger Educational Services, 1989, pp. 5–20 and 5–21, the content of which is expressly incorporated herein.

A simple power law has been found sufficient to fit published laboratory data for longitudinal relaxation time $T_1$ of methane gas, as well as log data. The expression used in accordance with the present invention is:

$$T_{1,g} = 25 \times 10^3 \, \rho/T^{1.17} \quad (5)$$

where $T_1$ is measured in seconds, the density $\rho$ in g/cm$^3$ and the absolute temperature T is in degrees Kelvin. Eq. (5) is valid for gas densities up to about 0.3 g/cm$^3$; higher densities generally approaching a liquefied gas state.

In accordance with the present invention the non-wetting oil phase relaxes with its bulk relaxation $T_{1,o}$, which is determined, for example, by using viscosity measurements of a sample. It has been determined that in order to successfully detect liquid hydrocarbons, for the $T_1$-weighted measurements in accordance with the present invention a long $T_1$ component (low viscosity) on the order of 1–2 s is necessary. The relatively large values for the parameter $T_1$ of light hydrocarbons provide a mechanism for distinguishing these fluids from water, since $T_1$ of water in rocks is almost always less than about 500 msec. In partially hydrocarbon-saturated water wet rock the hydrocarbon-water contrast is even better because $T_1$ (and $T_2$) of water are shorter, due to the fact that water typically resides in the smallest pores.

Figure 5B:
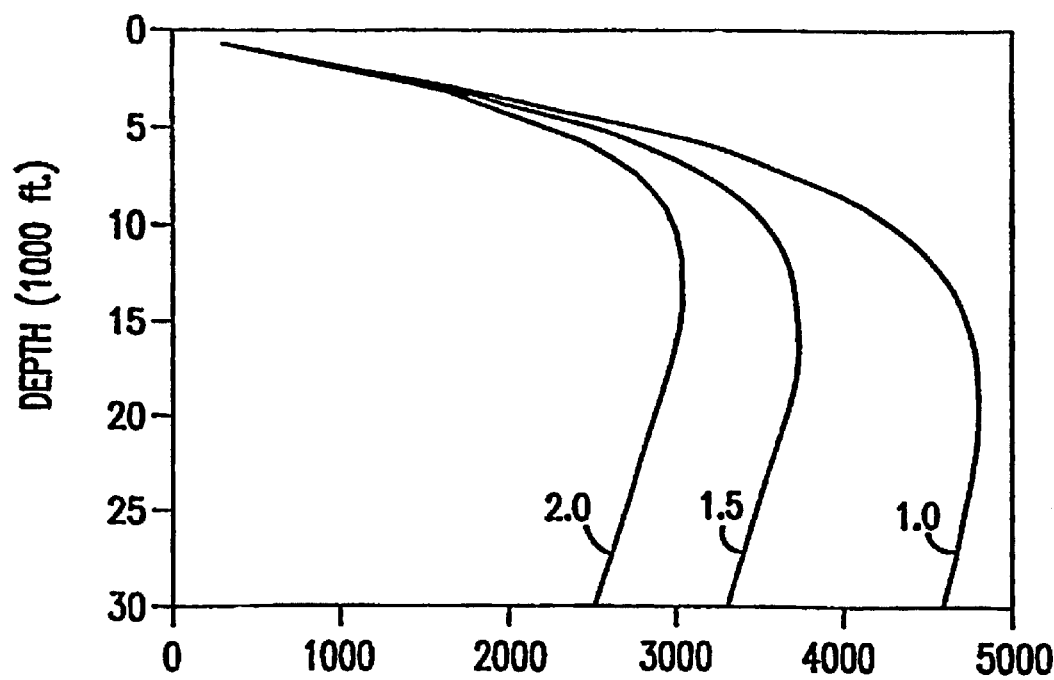
FIG. 5B shows the dependency of the longitudinal relaxation time $T_1$ as a function of depth at temperature gradients of 1, 1.5 and 2° F./100 ft, and pressure gradient of 43.3 psi/100 ft.
Figure 5C:
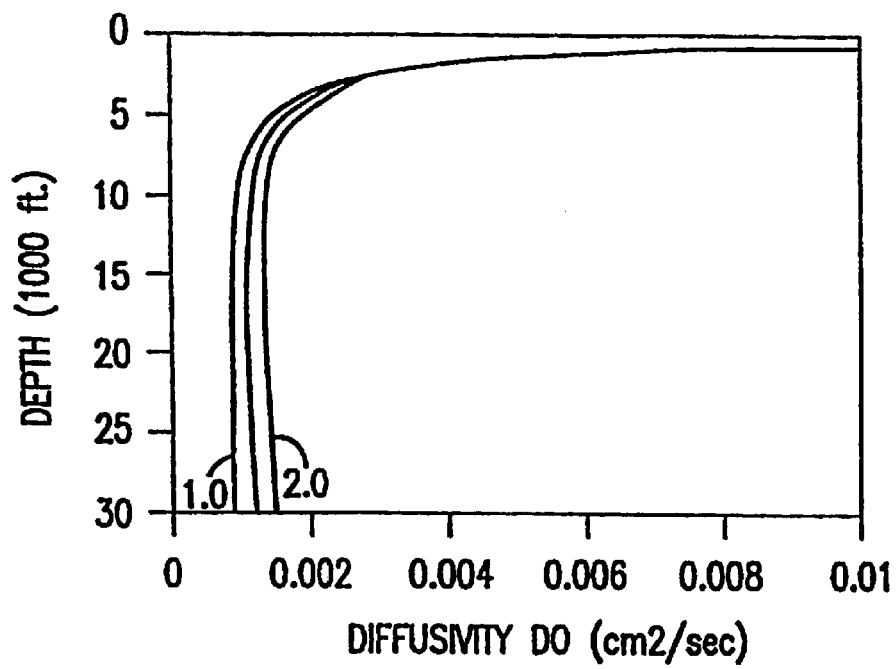
FIG. 5C shows the dependency of the self-diffusion coefficient $D_0$ of methane as a function of depth at temperature gradients of 1, 1.5 and 2°F./100 ft.
Figure 5D:
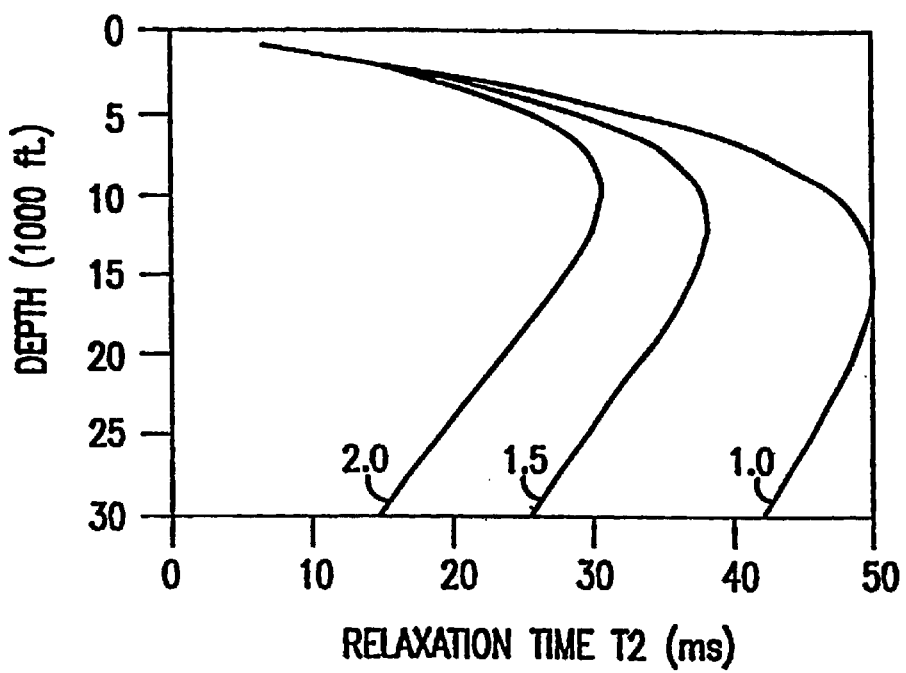
FIG. 5D shows the apparent transverse relaxation time $T_2^*$ based on diffusivity $D_0$ as in FIG. 5C, diffusion restriction $D/D_0$, and magnetic field temperature gradient of −0.18%/°C.
Figure 5E:
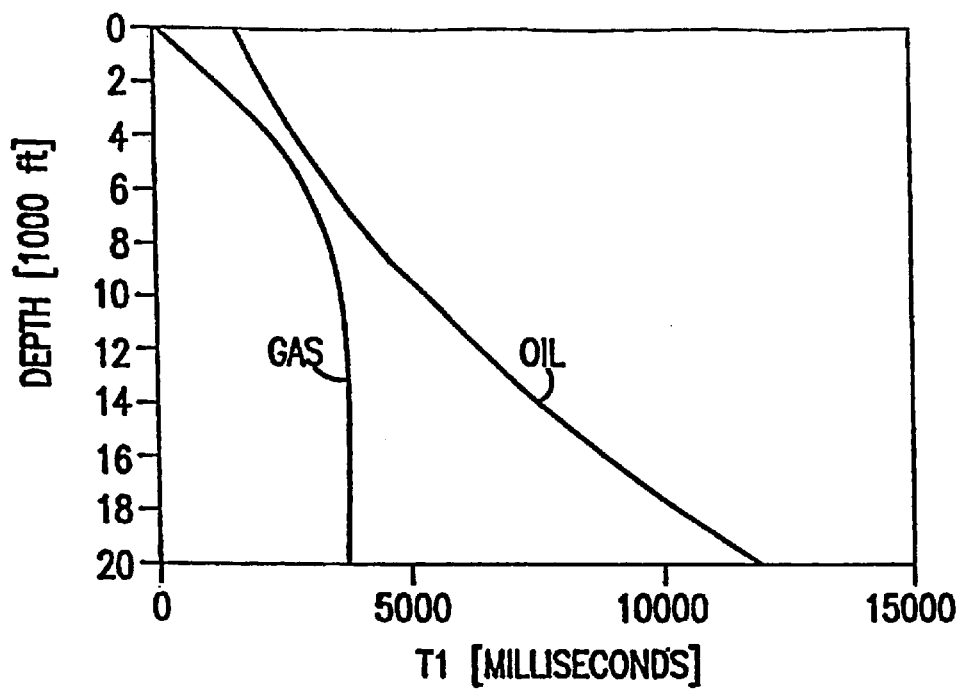
FIG. 5E shows values for the $T_1$ parameter of methane gas and light oils as a function of logging depth.

FIG. 5E shows, on the other hand, values for the $T_1$ parameter of gas (methane) and light oils at depths below 4000 feet. Both curves were computed assuming a geothermal gradient of 1.5° F./100 feet. The oil curve was computed assuming a temperature-dependent viscosity, using the expression $\eta = \eta_0 \exp(Q/RT)$, where $\eta_0 = 0.01$ cp, Q=10.5 kJ/mol and R=8.314 J/mol/K. As seen in the figure, due to different relaxation mechanisms, $T_1$ for methane can be relatively short, i.e., between about 2.5 and 4 seconds, while in the specific example $T_1$ for oil can be very long (on the order of 10 sec). Standard logging practice requires to set the wait time between successive CPMG pulse trains long enough for substantially fall recovery (about 95%) of the longitudinal magnetization. Accordingly, waiting times for a particular measurement have to be adjusted dependent on the specific oil.

The apparent diffusivity D of a fluid depends both on the self-diffusion coefficient $D_o$ and the restrictions imposed by the pore space. In accordance with a preferred embodiment of the present invention, an experimental temperature and density relationship for unrestricted gas diffusion $D_{0,g}$ is used, which can be expressed mathematically as:

$$D_{0,g} = 8.5 \times 10^{-7} \, T^{0.9}/\rho, \quad (7)$$

where $D_{0,g}$ is measured in cm²/s, the temperature T is measured in degrees Kelvin and the density $\rho$ in expressed in g/cm³. Below 7,000 ft, the opposing effects of temperature and pressure stabilize the diffusion parameter $D_0$ at a value of about $10^{-3}$ cm²/s. Diffusion restriction in the pore space should also be taken into account since the diffusion length (given by sqrt($2\tau D_0$)) is approximately equal to 10 μm. $D/D_0$ ratios in rock samples at this length scale have been observed ranging from about 0.55 (Indiana limestone) to about 0.9 (oomoldic limestone). Sandstone samples have been found to cluster in a tight $D/D_0$ ratio range of 0.7–0.8, which is consistent with experimental observations of $T_{2,g}^\dagger$ from log data.

Because of diffusion, the intrinsic relaxation rate $1/T_{2,g}$ for gas is negligible compared to $1/T_{2,g}^\dagger$ (see Eq. (3)). Similarly, the diffusivity of the oil phase is small compared to that of the gas phase. Consequently, the parameters $T_{2,o}$ and $T_{2,o}^\dagger$ which are used in the matched filter expression considered next are much larger than both $T_{2,g}^\dagger$ and also much larger than the total acquisition time required to separate oil from gas signals. As indicated above, numerical values for these parameters can be obtained, for example, from sample measurements.

Figure 5F:
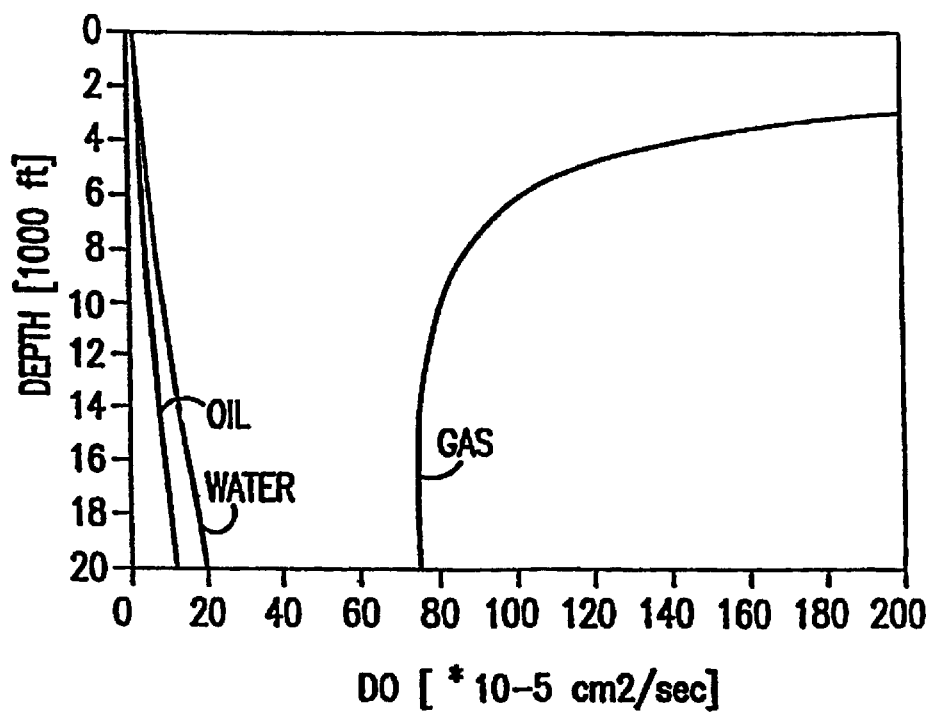
FIG. 5F illustrates the self diffusion coefficients $D_0$ for methane, water and light oil as a function of logging depth.
Figure 5G:
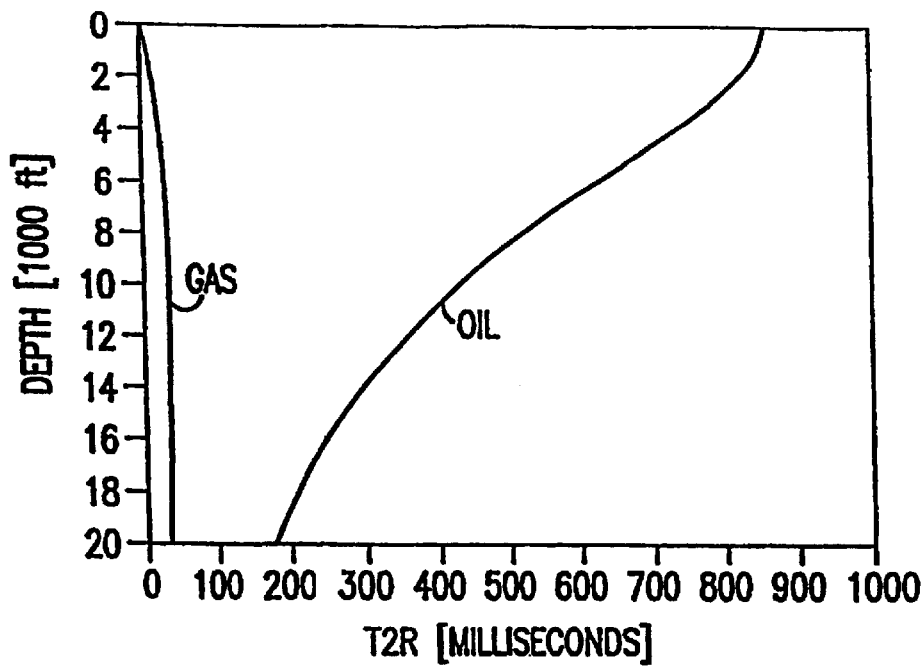
FIG. 5G illustrates the measured $T_{2R}$ for gas and oil as a function of logging depth.

FIG. 5F illustrates the self diffusion coefficients $D_0$ for methane, water and light oil. All curves are based on geothermal gradient of 1.5° F./100 feet, and (for gas) a hydrostatic pressure gressure. As seen, the methane $D_0$ is at least about 50 times larger than that of water and light oil. The resulting contrasts in the measured $T_2$ (i.e., $T_{2r}$) for gas compared to oil are shown in FIG. 5G. The plots include the effect of temperature and pressure on $T_1$ (see FIG. 5E) and D (see FIG. 5F) for both fluids and the effect of temperature on the parameter G for the tool. Moderate restriction diffusion effect on gas and no restriction effects on oil diffusion was assumed, i.e., $(D/D_0)_g = 0.7$; $(D/D_0)_o = 1$, Comparison of FIGS. 5E and 5G reveals that gas has a high ratio $T_1/T_2$ (larger than about 200) at all depths, which is a characteristic signature of gas. For light oil, however, this ratio is approximately equal to one and rises slowly with increased depth.

Table 2 summarizes expressions for the parameter estimates of different fluids used in accordance with a preferred embodiment of the present invention.

TABLE 2

| Fluid | Spin Lattice Relaxation (sec) | Self Diffusion coeff. (cm²/sec) | parameters/units |
|---|---|---|---|
| Methane | $T_{1,g} = 25.10^3 \, \rho/T^{1.17}$ | $D_{0g} = 8.5.10^{-7} T^{0.9}/\rho$ | Gas density $\rho$ in gramm/cc; T-abs temp in Kelvin |
| Oil | $T_{1,o} = 1.2(T/298)/\eta$ | $D_{0,o} = 1.3(T/298)/\eta$ | $\eta$ is oil viscosity in cp; T-abs temp in Kelvin |
| Water | $T_{1,w} = 3(T/298)/\eta$ | $D_{0,w} = 1.2(T/298)/\eta$ | Same as above |

For illustrative purposes, examples of pre-calculated values for $HI_g$ diffusivity and the relaxation time parameters $T_{1,g}$ and $T_{2,g}^\dagger$ as functions of depth are shown in FIGS. 5A to 5D. In particular, FIG. 5A shows the hydrogen index (HI) of methane as a function of depth at different temperature gradients; FIG. 5B shows the dependency of the longitudinal relaxation time $T_1$ as a function of depth at temperature gradients of 1, 1.5 and 2° F./100 ft, and pressure gradient of 43.3 psi/100 ft; FIG. 5C shows the dependency of the self-diffusion coefficient $D_0$ of methane as a function of depth; and FIG. 5D shows the apparent transverse relaxation time $T_2^\dagger$ based on diffusivity Do as in FIG. 5C, diffusion restriction $D/D_0$, and magnetic field temperature gradient of $-0.18\%/°C$.

In the examples shown in FIGS. 5A–D, a hydrostatic pressure gradient of 43.3 psi/100 ft and temperature gradients of 1, 1.5 and 2° F./100 ft were assumed, as shown. Additional parameters used in the examples include: frequency=72 OkHz, $\tau_{eff}$=0.65 ms and $D_g/D_{0,g}$=0.8. The tool and the formation temperature were assumed to be equal. It can be seen from FIGS. 5B and 5D that functionally the curves for $T_1$ and $T_2^\dagger$ are similar and that the ratio $T_1/T_2^\dagger$ stays within narrow limits for a wide range of temperatures and logging depth.

Data Acquisition

Figure 6:
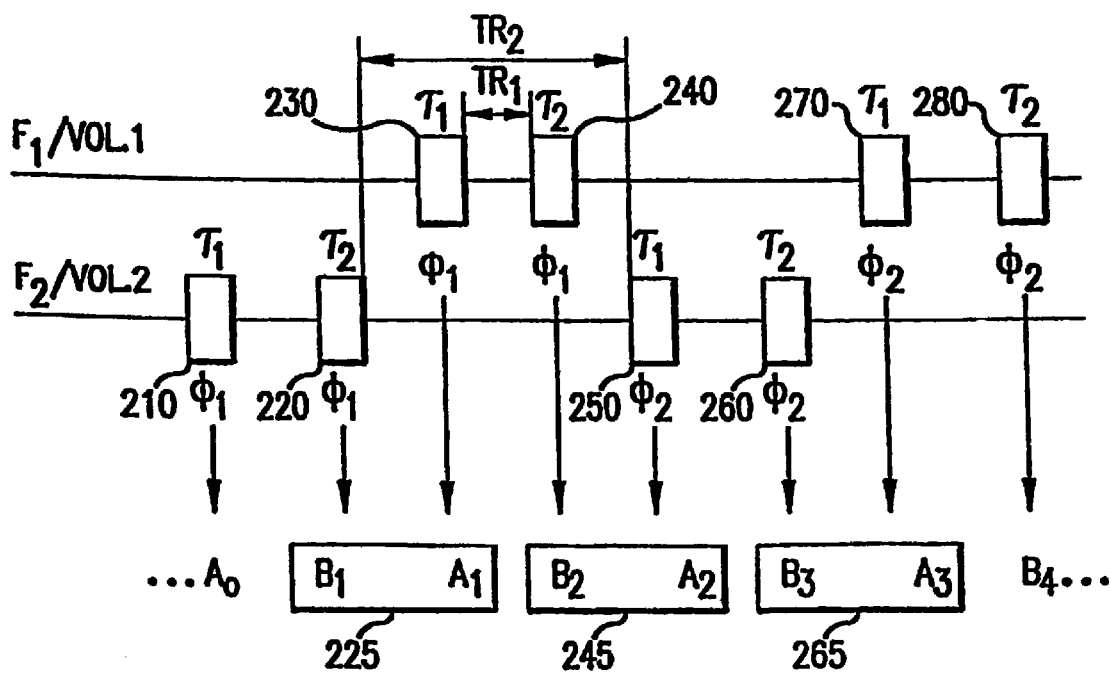
FIG. 6 is an illustration of an interleaved data acquisition pulse sequence for $T_1$ weighted and diffusion-weighted saturation recovery CPMG echo trains in a specific embodiment of the present invention using two tool frequencies.

As indicated above, the MRIL tool of the present invention is capable of performing separate, quasi-simultaneous measurements in different sensitive volumes by simply switching the operating frequency of the tool by a small amount. In accordance with a preferred embodiment of the present invention, this multi-frequency capability of the MRIL tool is used to provide a new data acquisition method which is particularly suitable for the detection of gas on the basis of NMR measurements with different recovery times $T_{Ri}$. To this end, with reference to FIG. 6, a novel interleaved pulse sequence is proposed in which at least two CPMG pulses 210 and 220 associated with resonant frequency $F_2$ are followed by at least two CPMG pulses 230, 240 associated with a different resonant frequency $F_1$. As shown in FIG. 6, the NMR measurement is continued next using at least two new pulses 250, 260 at the initial resonance frequency $F_2$, followed by at least two separate pulses 270, 280 at the $F_1$ frequency. Due to the fact that resonant frequency $F_1$ excites protons only in volume 1 of the formation and resonant frequency $F_2$ excites protons only in volume 2 of the formation, pairs 225, 245, 265, etc., of independent complex data points can be collected at each depth mark. As shown for illustrative purposes in FIG. 6, the first data point in each pair, generally designated as $B_i$ corresponds to a short recovery time $T_{R1}$, while the second data point, generally designated as $A_i$, corresponds to a long recovery time $T_{R2}$.

Thus, using the data acquisition sequence illustrated in FIG. 6, by "hopping" the resonance frequency $F_i$ of the tool, and alternating between adjacent resonant volumes of the formation one can obtain a sequence of signal pairs, each pair corresponding to substantially the same depth mark in the formation, but measured at different recovery times. It should further be noted that data for two different recovery times need not necessarily be obtained from only two different frequencies. For example, two or more measurements associated with different frequencies can be combined (i.e., averaged) to result in a single data stream corresponding to either a short, or a long recovery time. Furthermore, it should be clear that by using more than two resonance frequencies, and applying a correspondingly larger number of pulses in each resonant volume, the data acquisition method of the present invention can easily be extended to the more general case of M-tuple measurement data sets, each measurement point corresponding to a different recovery time $T_{Ri}$.

The interleaved multi-frequency data acquisition method described above is clearly preferable to prior art methods which require separate logging passes, because it provides a simple approach to dealing with depth alignment problems. Preferably, the pulse sequences in FIG. 6 systematically alternate the roles of all sensitive volumes (and pulse phases) in order to negate any systematic difference between operating frequencies.

The data acquisition method was described above with reference to identical CPMG sequences, which mode is referred to in the present application as $T_1$-weighted acquisition. Data from this acquisition mode is suitable for the Differential Spectrum Method (DSM) described in the Akkurt et al. paper. Notably, however, the method is also suitable for direct signal subtraction in the time domain, as described in more detail next.

In an alternative preferred embodiment of the present invention, a novel data acquisition mode referred to as $T_1$- and diffusion-weighted acquisition can also be used. As indicated above with reference to the SSM method, the contrast between liquid and gas signals can be enhanced by using a slightly larger pulse-echo spacing for the CPMG train associated with the shorter recovery interval. This embodiment is illustrated in FIG. 6 using two different intervals $\tau_i$ for each successive pulse in the same resonance volume. It has been found, however, that it is not necessary to eliminate the gas signal altogether. For example, an increase by only 40% in the pulse echo $\tau$ has been found to cause a 50% decrease in the diffusion-induced part of $T_2$. As indicated above with reference to the SSM method, because of diffusion dominance, the effect is much more pronounced for gases than for liquids, and can accordingly be used to enhance the separation of the two phases.

In another aspect of the invention, a modified pulse sequence is disclosed preferably for use with low field gradient tool measurements. The key idea is to use a modified CPMG (Carr-Purcell-Meiboom-Gill) sequence that is characterized by two echo spacings. The first echo is subject to a variable echo spacing TD; ranging from approximately 1 ms to hundreds of milliseconds. With such a large range possible for TD, the diffusion characteristics of the fluid(s) involved can be made a dominant factor for amplitude decay. The second and all following echoes are generated with short spacings (TE, typically 1 msec). In this period, the influence of diffusion is negligible in a low field gradient, and a dense sampling regime is maintained, resulting in good sensitivity. The amount of amplitude loss incurred in the TD interval is directly related to the diffusivity of the hydrogen-bearing fluids. TD is a parameter that varies from a low of TE (i.e. a simple CPMG sequence) to highs of hundreds of milliseconds.

Figure 12A:
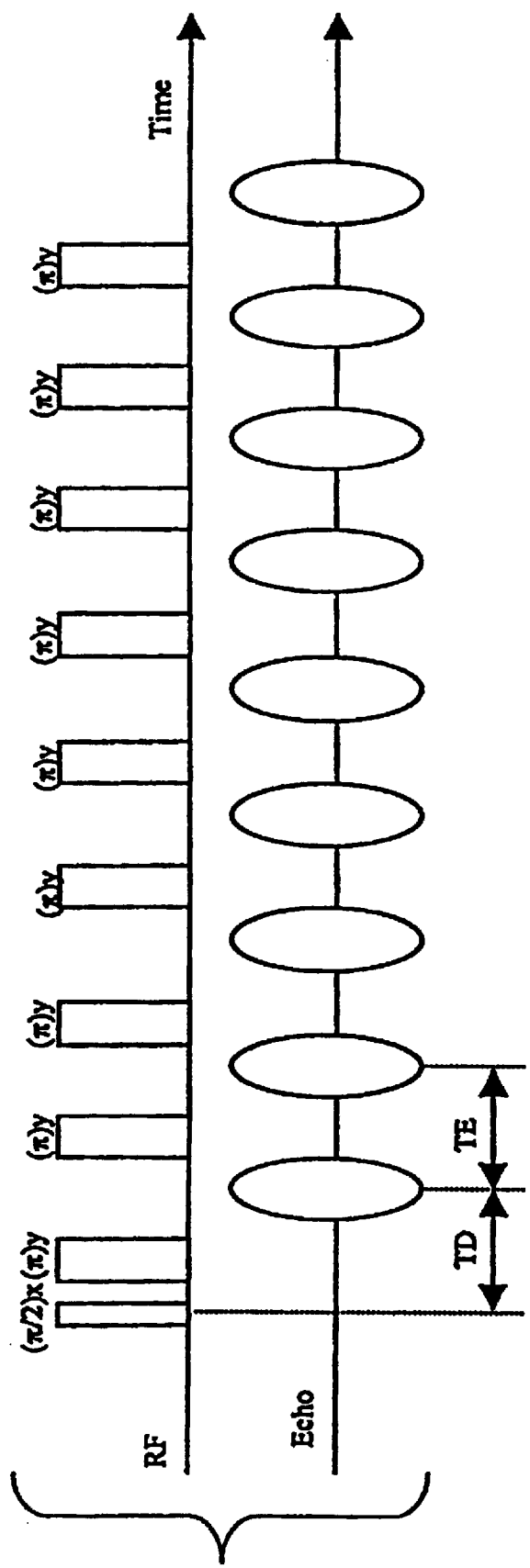
FIGS. 12A–C illustrate a modified pulse sequence used in accordance with the present invention for low field gradient magnetic tools.
Figure 12B:
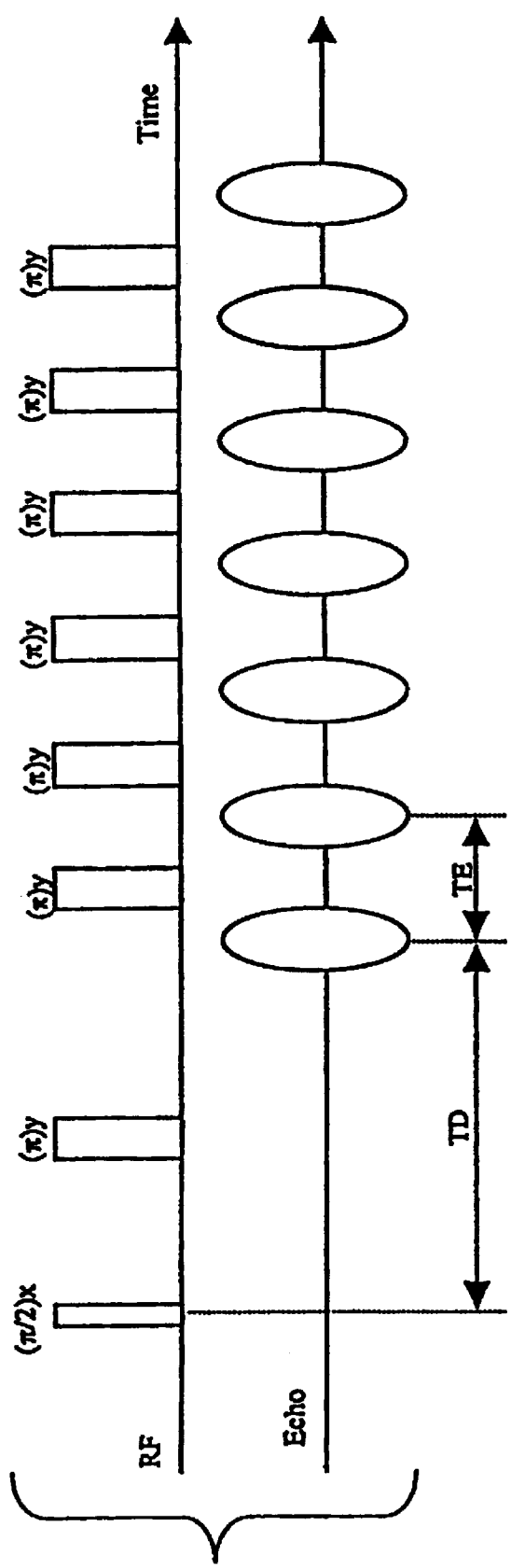
Figure 12C:
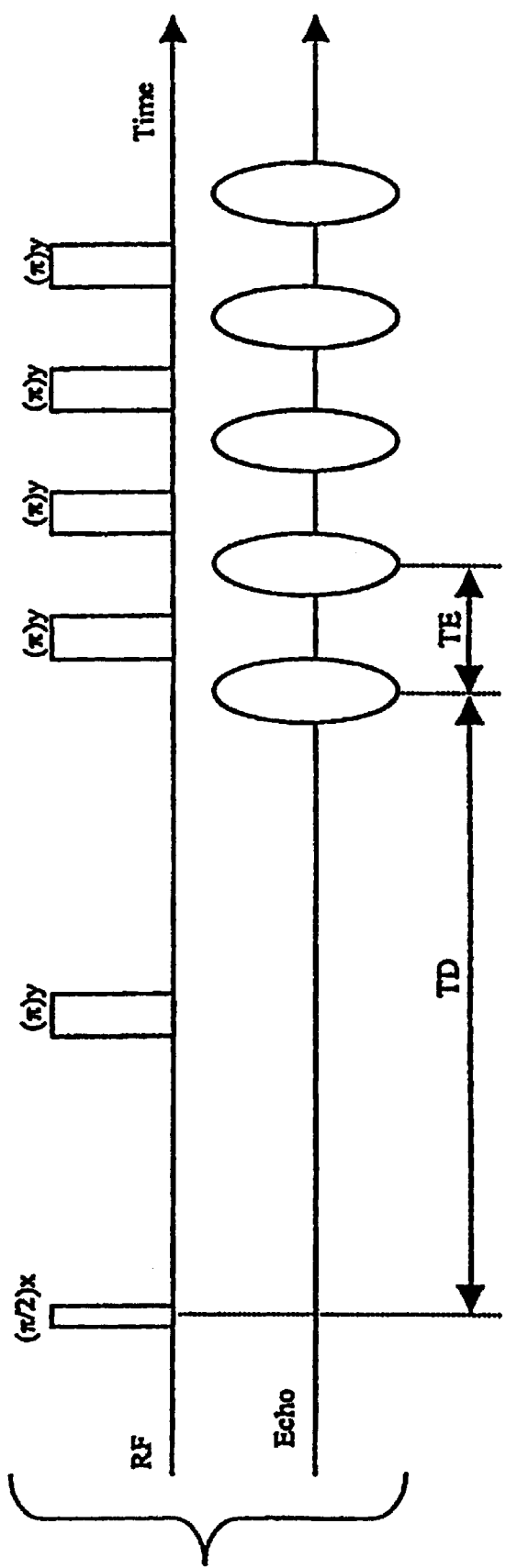

An example of the sequence used in a preferred embodiment is shown in FIGS. 12A–C. In particular, FIG. 12A illustrates the trivial case of TD=TE, which is a standard CPMG sequence used as a reference. The TE interval is chosen short enough, such that the influence of diffusion on the echo amplitude decay is negligible. As shown in FIGS. 12B and 12C, in accordance with this aspect of the invention the TD interval is increased in successive measurements. In a preferred embodiment, the granularity of the TD interval is chosen such that the later echoes line up in time with those of the CPMG scan and a one-to-one correspondence can be established. In a preferred embodiment, the second TD value can be chosen to attenuate or eliminate signals from the gas phase only. The difference between corresponding echoes (as shown in FIGS. 12A and 12B) would therefore be signal corresponding to the presence of gas. In accordance with the preferred embodiment the third TD value can be selected to attenuate or eliminate both gas and free water signals. Accordingly, the remaining signal (illustrated in FIG. 12C) could come only from the oil phase, which typically has the slowest self-diffusion rate.

Selection of the TD interval

The echo attenuation during the TD and TE intervals used in accordance with the present invention is given by the classic expression for a CPMG sequence:

$$A(t)=A_0 \exp(-1/12(gGTx)^2 D\, t),$$

where A is the echo amplitude, g is the gyromagnetic ratio, G is the field gradient, Tx is the interval TD or TE, respectively, and D is the self-diffusion constant. For the purpose of this discussion, spin-lattice and spin-spin relaxation are ignored for the moment. To illustrate the method, the following values can be used:

| | |
|---|---|
| $D = 10^{-3}$ cm$^2$/s | for the vapor (gas) phase, |
| $D = 10^{-4}$ cm$^2$/s | for the free-water phase, and |
| $D = 10^{-5}$ cm$^2$/s | for the oil phase. |
| TE = 0.001 sec, | |
| G = 1 gauss/cm, | |
| g = 2p4258 sec$^{-1}$/gauss | |
| (proton gyromagnetic ratio). | |

It will be appreciated that other values can be selected in different applications. With the above assumptions, in the TE interval and in the case TD=TE, even for the fastest diffusion case, the diffusion-induced signal decay rate is only:

$$1/12(2p4258 \times 1 \times 0.001)^2\, 10^{-3}\, \text{sec}^{-1} = 0.06\, \text{sec}^{-1},$$

which is small compared to typical intrinsic $T_2$ rates (~0.25 sec$^{-1}$) and typical pulse-echo train lengths (~1 sec). Therefore, in accordance with this aspect of the invention during the TE interval the influence of diffusion can be ignored. Further, it will be appreciated that the case TD=TE can serve as a reference without echo attenuation due to diffusion.

In accordance with the present invention, the next TD value should attenuate the gas signal by approximately 86%

(i.e., two time constants). It follows that TD should obey the following equation:

$$2 = 1/12(gGTD)^2 \, D \, TD, \text{ with } D=10^{-3} \text{ cm}^2/\text{s and } G=1 \text{ gauss/cm}.$$

It follows that $$TD^3 = 24/(g^2G^2D) = 24 \times (2p4258)^{-2} \times 1 \times 10^3, \text{ or } TD = 0.032 \text{ sec}.$$

The amplitude of the free-water signal is attenuated by a factor of $$\exp(-1/12(gG \, 0.032)^2 \times_{10}^{-4} \times 0.032) = 0.82.$$

The echo train with TD=32 ms contains 14% of the gas signal, 82% of the free-water signal and 98% of the oil signal (from an analogous calculation). An echo-by-echo subtraction from the TD=1 ms train isolates the gas signal as follows: 86% gas signal, 18% free-water signal and 2% oil signal. The bound-water signal is eliminated by considering only echoes that occur after 32 ms.

For the current example, a third TD value is chosen equal to 70 ms to isolate the oil signal. In this case, the gas signal is completely eliminated, the free-water signal is attenuated by 86% and the oil signal remains at 82% of its value.

The TD interval selection used in accordance with the preferred embodiment can be summarized as follows:

| TD value | results in signals from... |
|---|---|
| 1 ms (=TE) | all fluid phases, weighted only hydrogen density and incomplete polarization (in case of short wait times), |
| 32 ms | free water, oil and some bound water (attenuated by intrinsic $T_2$), |
| 70 ms | oil only (attenuated by intrinsic $T_2$). |

It will be appreciated that the above values are used as guidelines only and can be replaced in practical application using the described computation techniques.

Signal Processing

In a first aspect, the method for fluid detection in accordance with a preferred embodiment of the present invention assumes data acquisition in the presence of a static magnetic field gradient in the range 10–30 G/cm. The method further requires at least two separate measurements with different saturation-recovery times $T_{Ri}$ and/or different echo-to-echo spacings, and is implemented using the data acquisition sequence illustrated in FIG. 6. In addition, the very low signal-to-noise (SNR) levels which are due to HI losses and incomplete magnetization recovery in a typical NMR measurement necessitate signal detection using two-channel complex data stream. Therefore, in a preferred embodiment of the present invention data is acquired in two orthogonal channels, and averaged over a vertical logging interval to increase the SNR for the acquired measurement data.

Figure 7:
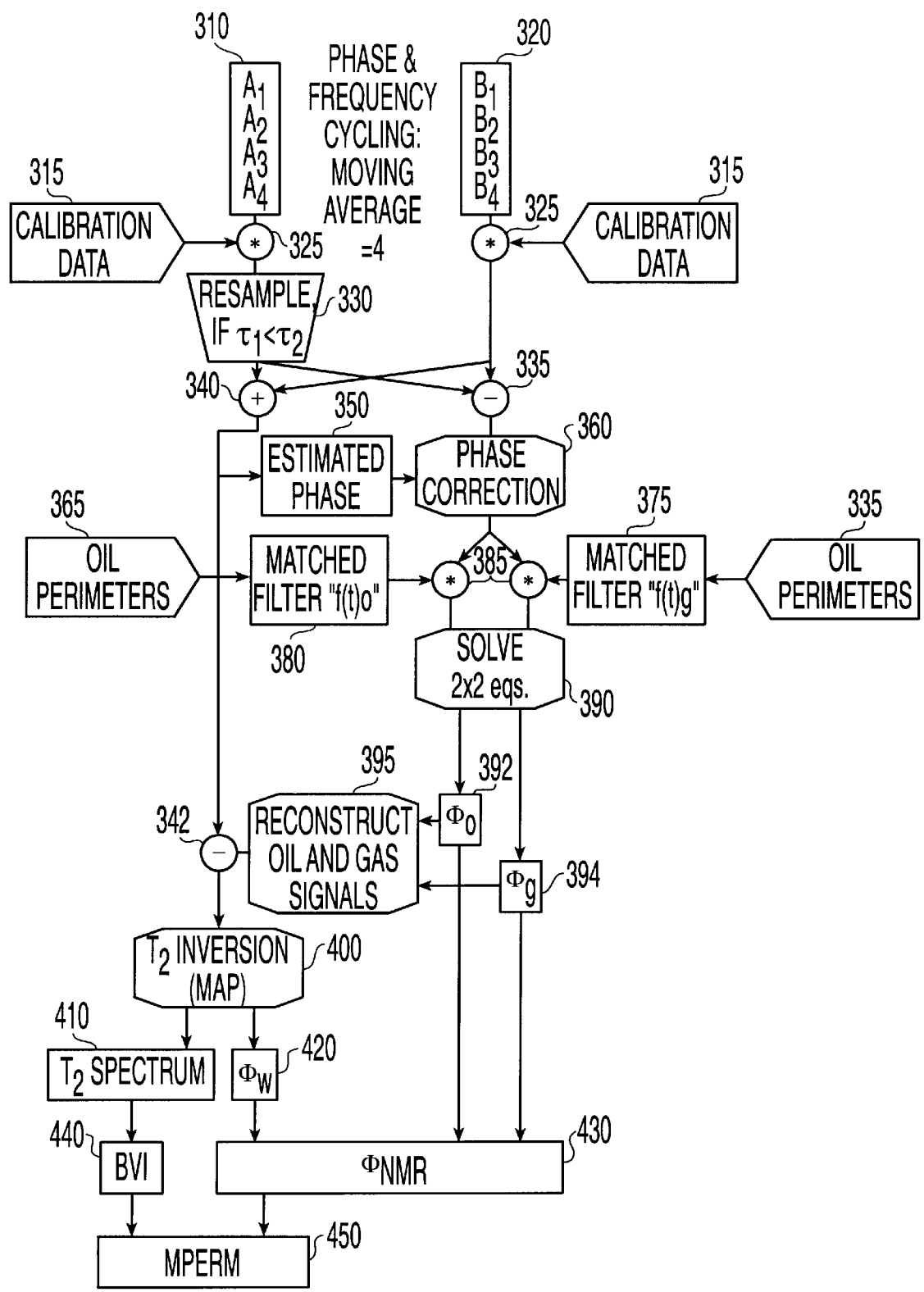
FIG. 7 is flow diagram of the data processing method in accordance with a referred embodiment of the present invention.

Turning next to FIG. 7, it shows in semi-block diagram form the signal processing method in accordance with a preferred embodiment of the present invention. Specifically, the determination of water, oil and gas saturations in the sensitive volume begins by performing at least two interleaved $T_1$-weighted measurements to separate the wetting phase (brine, surface-dominated relaxation) from the non-wetting phase (light hydrocarbons, bulk-dominated relaxation). Optionally, these measurements can be diffusion-weighted as well. As shown in FIG. 7, this results in two parallel data sets of complex time-domain data. Data sequence 310 generally corresponds to data obtained from the long recovery time $T_{R2}$, while data sequence 320 corresponds to data obtained from the short recovery time $T_{R1}$. Between about 150 and 300 data points are used in each sequence. Preferably, the recovery times used are about 2 sec for $T_{R1}$ and about 8 sec for $T_{R2}$. Pairs of echo trains are formed by matching overlapping short and long TR intervals thereby minimizing the systematic variations introduced when formation bed boundaries are crossed.

Figure 8A:
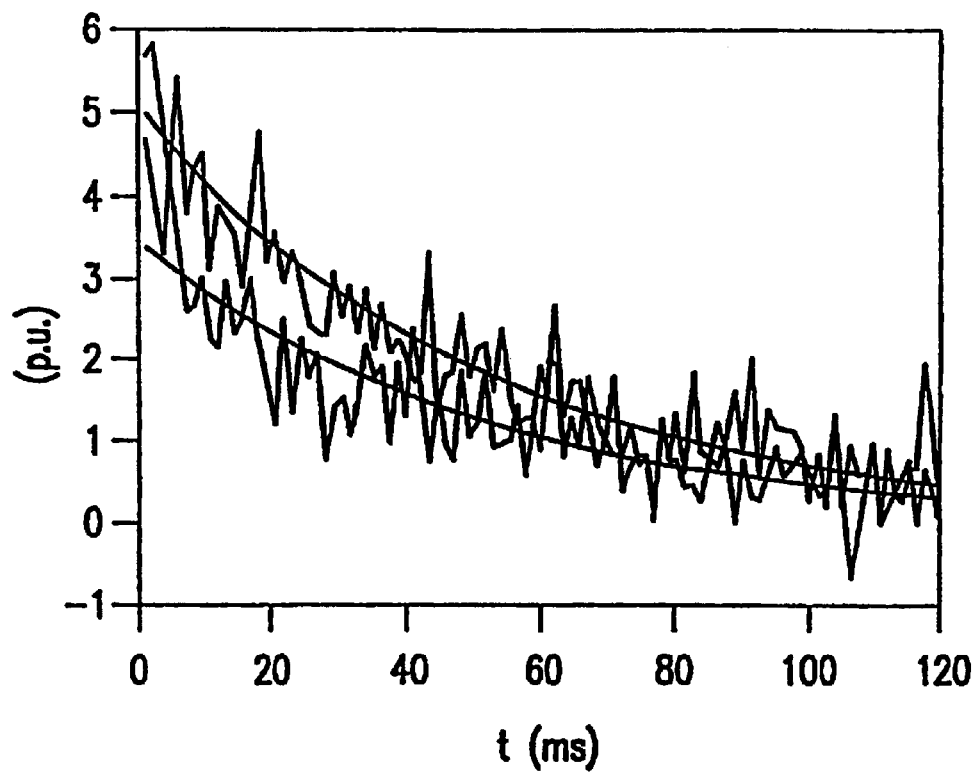
FIG. 8A illustrates the difference between two signals with different recovery times $TR_i$.

Following the data acquisition process, in block 325 the two data sets are corrected using calibration data from blocks 315. Specifically, such calibration data is obtained from samples at room temperature, with 100% water saturation, for example in a water-filled tank. FIG. 8A shows two such calibrated data sequences as functions of time. As shown in FIG. 8A, the magnitude values for the measurement signals are conveniently calibrated in porosity units (p.u.). Skipping for a moment block 330, next the complex difference between the signals in each data pair is obtained in subtractor 335 to eliminate the brine contribution; the sum signal is obtained in adder 340 to estimate the input signal phase and phase-correct the difference signal in block 335 accordingly. Specifically, it has been observed that while the absolute phase of the NMR signal is subject to slow variations due to hole and tool conditions, it shows excellent short-term stability. Therefore, the phases of the sum and the difference signals are approximately equal. In accordance with the present invention this feature is used to correct the phase of the difference signal on the basis of a phase estimate for the sum signal which was found to be comparatively more accurate.

In particular, a depth-averaged signal phase is computed in block 350 from the complex sum signal. If proper frequency and phase cycling has been employed during data acquisition, all sum and difference echoes have the same average phase. The phase estimated in block 350 is used to rotate, in phase correction block 360, the phase of all data points in the complex difference signal into the real axis. Such rotation yields the true absorption mode (real-valued) signal component. The dispersion signal component (imaginary valued) can be discarded.

Based on the parametric representations for relaxation times and diffusion characteristics of the non-wetting hydrocarbon phases which are computed, as indicated in the section "Signal Modeling and Corrections", and stored in block 365 for the oil and block 370 for the gas components. Matched filters representing the liquid and the gaseous phases are computed next in blocks 375, 380 in the echo-time domain, using the expressions:

$$f(t)_o = [\exp(-TR_1/T_{1,o}) - \exp(-TR_2/T_{1,o})]\exp(-t/T_{2,o}), \quad (7a)$$

$$f(t)_g = HI_g[\exp(-TR_1/T_{1,o}) - \exp(-TR_2/T_{1,o})]\exp(-t/T_{2,o}^*) \quad (7b)$$

where all used parameters have been pre-computed.

In general, the filter functions in Eqs. (7a–7b) are not orthogonal and cannot be directly applied to the data. (See FIG. 9A) Instead, the amplitude responses to these filters are extracted from the phase-corrected difference signal d(t) by solving, in block 390, the overdetermined equation system, $$Ax = d(t), A = [f(t)_o^T \, f(t)_g^T] \quad (8)$$

in a least-squares sense. The solution is found by solving the following 2×2 equation system for the amplitude vector x:

$$(A^T A)x = A^T d(t), \quad (9)$$

If the difference signal d(t) was properly scaled in p.u., the first element of the solution vector x is oil-filled porosity $\Phi_o$, obtained in block 392, and the second is gas-filled porosity $\Phi_g$ (block 394). Calculating backwards from these numbers, the properly scaled oil and gas signatures can be reconstructed in block 395, and subtracted from the complex sum signal in block 342. The remainder is the signal originating from brine, which, as wetting phase, is sensitive to the surface-to-volume ratios in the remaining pore space available to water.

In block 400, a $T_2$ inversion mapping is constructed, as discussed, for example in the Prammer et al. paper above. The results are used, in block 410, to estimate the $T_2$ spectrum of the signal and in block 420 to estimate the water-bound porosity.

These ratios are indicative of the non-producible water volume held in place by capillary forces (BVI), which is computed in block 440. On the other hand, the total area under the $T_2$ curve is interpreted as water-filled porosity $\Phi_w$, which is computed in block 420. The total NMR porosity can be computed in block 430 using the expression:

$$\Phi_{NMR} = \Phi_w + \Phi_o + \Phi_g \qquad (10)$$

The free-fluid index as seen from the water phase is augmented by oil and gas porosity:

$$FFI = FFI_w + \Phi_o + \Phi_g \qquad (11)$$

From $\Phi_{NMR}$, BVI and FFI, a permeability estimate can be calculated in block 450, which depends only on NMR-derived quantities.

Processing of Diffusion-weighted Data

Turning back to block 330 in FIG. 7, for a diffusion-weighted measurement a complication arises from the different sampling grids employed in acquiring the data sets which make up a data pair. In this case, data from the shorter echo spacing is mapped onto the wider sampling grid by linear interpolation between complex echoes. Diffusion-weighting is taken into account to give the following matched-filters expressions:

$$f(t)_o = [\exp(-TR_1/T_{1,o}) - \exp(-TR_2/T_{1,o})]\exp(-t/T_{2,o}), \qquad (12a)$$

$$f(t)_g = HI_g[1-\exp(-TR_2/T_{1,g})]\exp(-t/T_{2,g}\dagger) - HI_g[1-\exp(-TR_1/T_{1,g})]\exp(-t/T_{2,g}\dagger(\tau_2/\tau_1)^2) \qquad (12b)$$

The diffusion-weighted data is next processed following the flow graph in FIG. 7. The combined $T_1$-weighted and diffusion-weighted measurement is advantageously used in cases where the gas filled porosity and HI are relatively low, and correspondingly the SNR of the measurement is relatively low.

Error estimates for $T_1$-weighted and diffusion-weighted data acquisitions in accordance with a preferred embodiment of the present invention can be obtained using the following considerations. The input data consists of two data sets, weighed by different recovery times and possibly sampled with different echo spacings. Each set is individually calibrated for HI=1.0. To compute the uncertainty of the parameter estimates, it is assumed that the noise in each data set is random and has Gaussian distribution with standard deviation $\sigma=\sqrt{2}$. As indicated in blocks 350 and 360 above, a depth-averaged signal phase is computed from the complex second echo in the sum. The estimated phase is used to rotate all complex differences into the real axis. Allowing for a small error in phase estimation, the noise component in the real-valued difference signal (dt) is approximately 1.5 p.u. Gas and oil porosities are given as least-squares solutions in block 390 in FIG. 7. Formally, the least-squares solution can be written as:

$$x_{(LSQ)} = (A^T A)^{-1} A^T d(t) \qquad (13)$$

Figure 10:
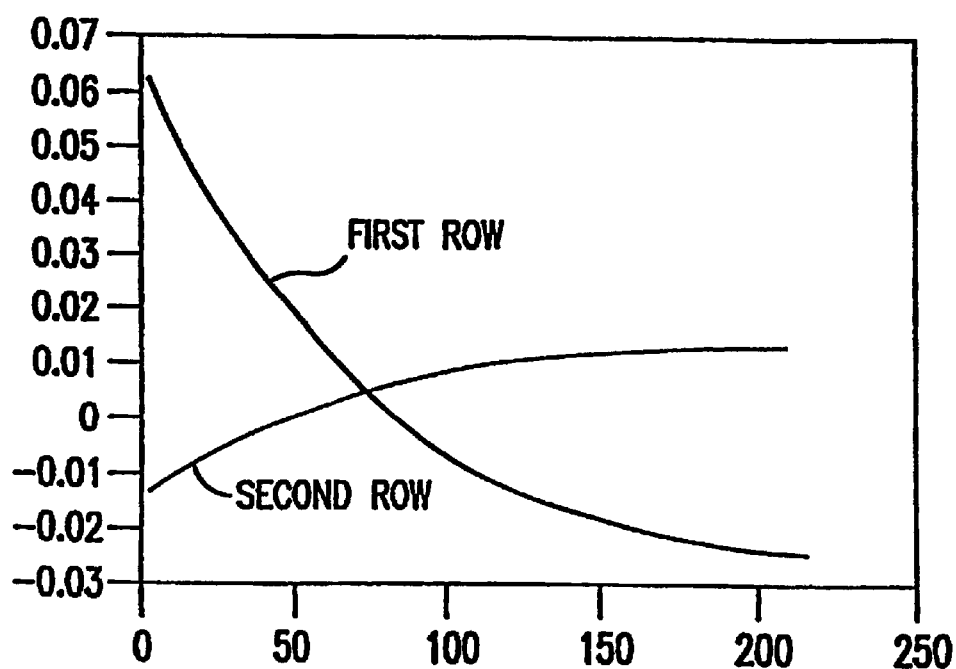
FIG. 10 shows orthogonalized filter functions of the gas and the oil matched filters in accordance with the present invention.

The sensitivity of the solution to random errors in the input is given by the condition number of the square, positive-definite matrix $A^T A$. The orthogonalized oil-sensitive filter function $f(t)'$, is the first row of the expression $(A^T A)^{-1} A^T$. The second row of this expression contains the orthogonal filter $f(t)'_g$, which is sensitive to the gas component. The orthogonal filter responses are shown in FIG. 10. Filter response functions are computed as follows:

$$\Phi_o = \int_0^\infty d(t)(f(t))'_o dt$$

$$\Phi_g = \int_0^\infty d(t)(f(t))'_g dt$$

The average output uncertainty was determined by Monte Carlo simulation. Using 100,000 samples, and assuming parameters, $HI_g=0.5$, $T_{1,g}=5$ s, the standard output deviation in the answer for gas filled porosity is $\approx 2.5$ p.u. The uncertainty in oil-filled porosity is substantially reduced and is approximately equal to 1 p.u., dependent on $T_{1,o}$.

As noted, in another aspect the invention uses low field gradient tools resulting in reduced static field gradients on the order of 0.3–3 gauss/cm. The modified processing sequence illustrated in FIGS. 12A–C is used in such case in a preferred embodiment.

For the reader's convenience, a list of all notations used in the description above is given next.

Nomenclature

A=design matrix for least-squares problem
$A^T$=transpose matrix of A
BVI=bulk volume irreducible water, p.u.
D=restricted diffusivity, $cm^2/S$
$D_o$=unrestricted diffusivity, $cm^2/S$
d(t)=difference function
f(t)=filter function
FFI=free fluid index, p.u.
G=magnetic field gradient, G/cm
HI=hydrogen index, relative to water
MPHI=apparent NMR porosity, p.u.
T=absolute temperature, ° K.
$T_1$=longitudinal relaxation time, s
$T_1^\dagger$=pseudo transverse relaxation time, s
$T_2$=transverse relaxation time, s
$T_2^\dagger$=apparent transverse relaxation time, s
TE=CPMG echo-to-echo delay (TE=2τ), s
TR=recovery time, s
x=solution vector to least-squares problem
$\Phi$=porosity, p.u.
$\Phi_{NMR}$=corrected NMR porosity, p.u.
$\Phi_n$=CPMG phase, n=1 or 2
γ=gyromagnetic ratio, $rad^{-1}G^{-1}$
ϱ=density, $g/cm^3$
σ=standard deviation
τ=CPMG pulse-to-echo delay (τ=TE/2), s
$\tau_{eff}$=diffusion-effective CPMG delay, s Subscripts g=gas
o=oil The following figures serve to provide better understanding of different aspects of the invention with reference to signals obtained in different processing blocks in FIG. 7.

Figure 8B:
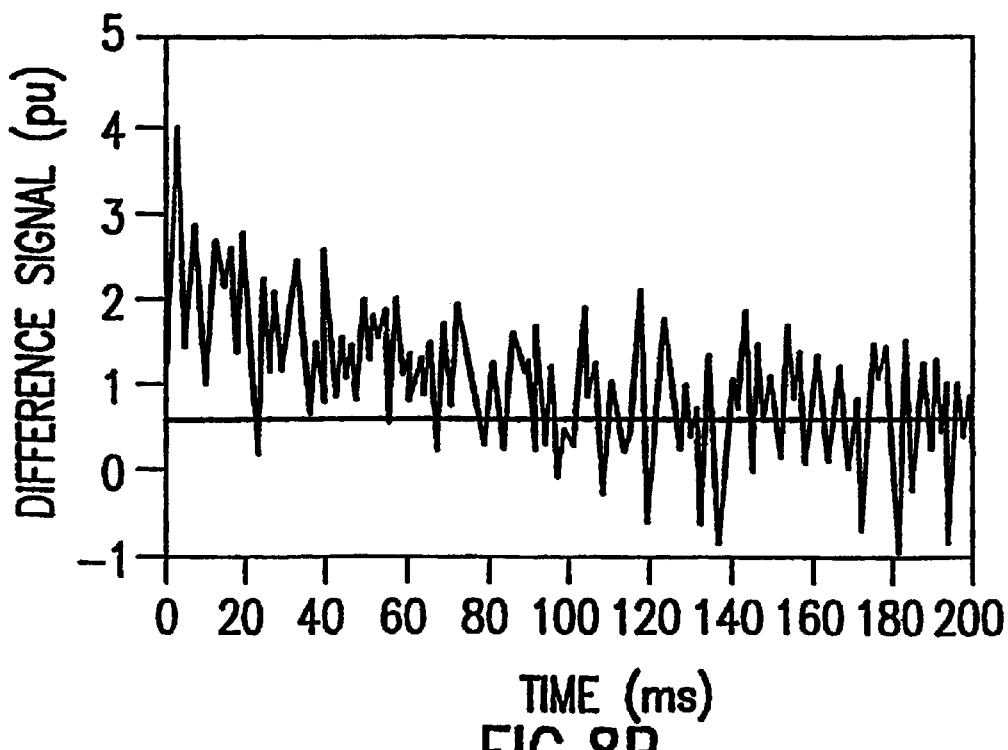
FIG. 8B shows a sample display of a difference data signal acquired at depth 15710 ft, as a function of time.
Figure 8C:
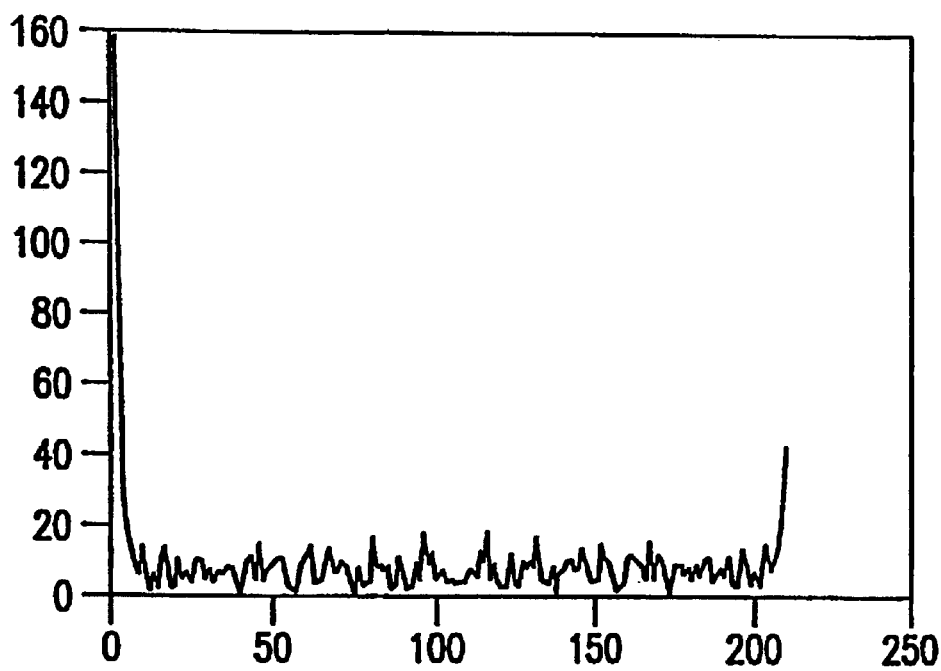
FIG. 8C is the magnitude of the Fourier transform of the signal shown in FIG. 8B.

In particular, FIG. 8A illustrates the difference between two signals with different recovery times $TR_i$. FIG. 8B shows a sample display of a difference data signal obtained at depth 15710 ft, as a function of time. FIG. 8C is the magnitude of the Fourier transform of the signal shown in FIG. 8B.

Figure 9A:
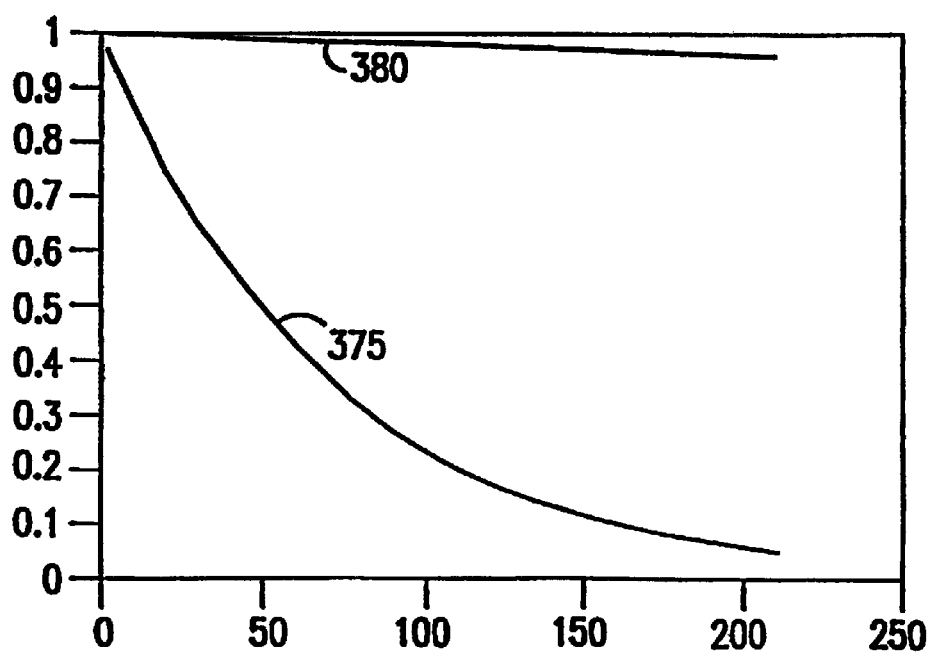
FIG. 9A shows sample response of the gas and the oil matched filters in accordance with the present invention.
Figure 9B:
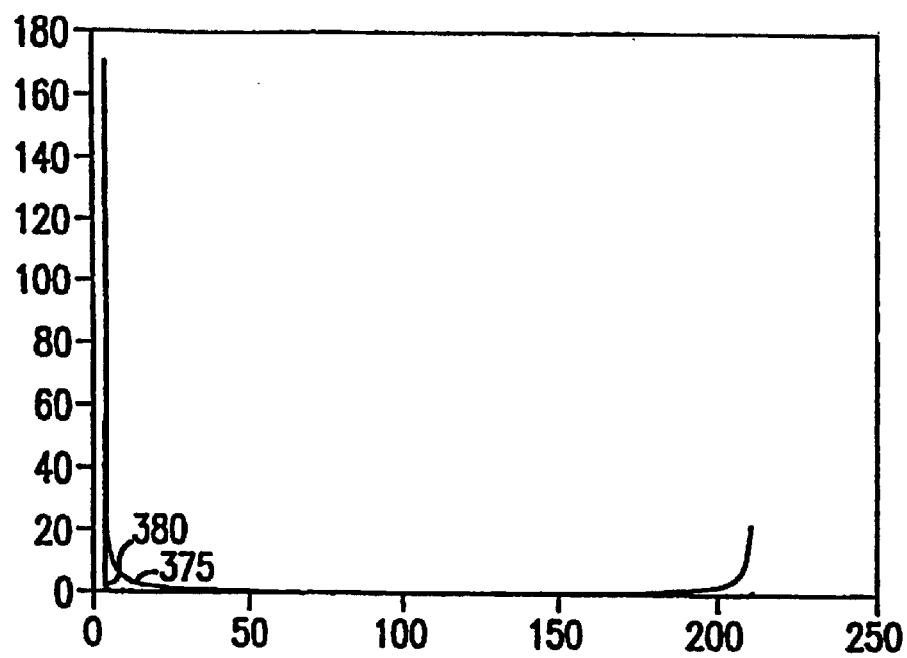
FIG. 9B is the magnitude of the Fourier transform of the matched filter responses shown in FIG. 9A.

FIG. 9A shows the response of the gas (block 375) and the oil (block 380) matched filters in accordance with the present invention; FIG. 9B illustrates the magnitude of the Fourier transform of the matched filters responses shown in FIG. 9A.

FIG. 10 shows the orthogonalized filter functions of the gas and the oil matched filters in accordance with the present invention.

Results

Logging tests were performed in single-frequency and dual frequency operating modes to assess the amount of vertical and lateral motion, which could affect the accuracy of the $T_1$-weighted measurements conducted in accordance with the present invention. A similar operating procedure was already in place to set the optimum delay time between measurements in the pay zone. Data acquired under a variety of hole conditions and $T_1$ values were examined; logging speeds in this particular mode were typically 300 ft/hr. In all cases, increasing the recovery time interval resulted either in a monotonic increase in NMR amplitude or in no increase. Sudden increases in amplitude at short recovery intervals, indicative of uncontrolled tool motion, were not observed.

The effect of invasion was studied by comparing results from wells drilled with water-base muds (WBM) and oil-muds (OBM). The WBM-drilled formations generally suffer high invasion and residual oil and gas saturations are low. Nevertheless, in many cases gas quantities above the detectability threshold are present, possibly due to backsaturation of gas into the invaded zone. As indicated above, another factor aiding the MRIL® is the 4" blind zone into the formation. OBM filtrate generally invades less and is therefore better suited for near-borehole saturation measurements. Oil filtrate mixes with the connate oil and replaces it to a certain extent. Because the filtrate has low viscosity, OBM aids the described hydrocarbon detection method by supplying a slowly relaxing component with known $T_1$. We recommend performing $T_1$ and $T_2$ measurements of filtrates in the laboratory at 1 MHz to assess the effect of OBM invasion.

The following example data was acquired in a deep (>10,000 ft), on-shore gas well, drilled with OBM. The gas parameters are summarized in Table 3.

TABLE 3 parameters for example data.

| | |
|---|---|
| gas temperature: | 100° C. |
| gas pressure: | 9000 psi |
| gas type: | $CH_4$ |
| $CH_4$ density: | $\rho = 0.26$ g/cm$^3$ |
| $CH_4$ hydrogen index: | $HI_g = 0.6$ |
| longitudinal relaxation time: | $T_1 = 6s$ |
| unrestricted diffusivity: | $D_0 = 0.7 \times 10^{-3}$ cm$^2$/s |
| diffusion restriction (est.): | $D/D_0 = 0.8$ |
| magnetic field gradient | $G = 18$ G/cm |
| effective pulse-echo spacing: | $\tau_{eff} = 0.65$ ms |
| apparent transverse relaxation: | $T_2^\dagger = 60$ ms |
| $T_1/T_2^\dagger$ contrast: | ~100 |

Figure 11:
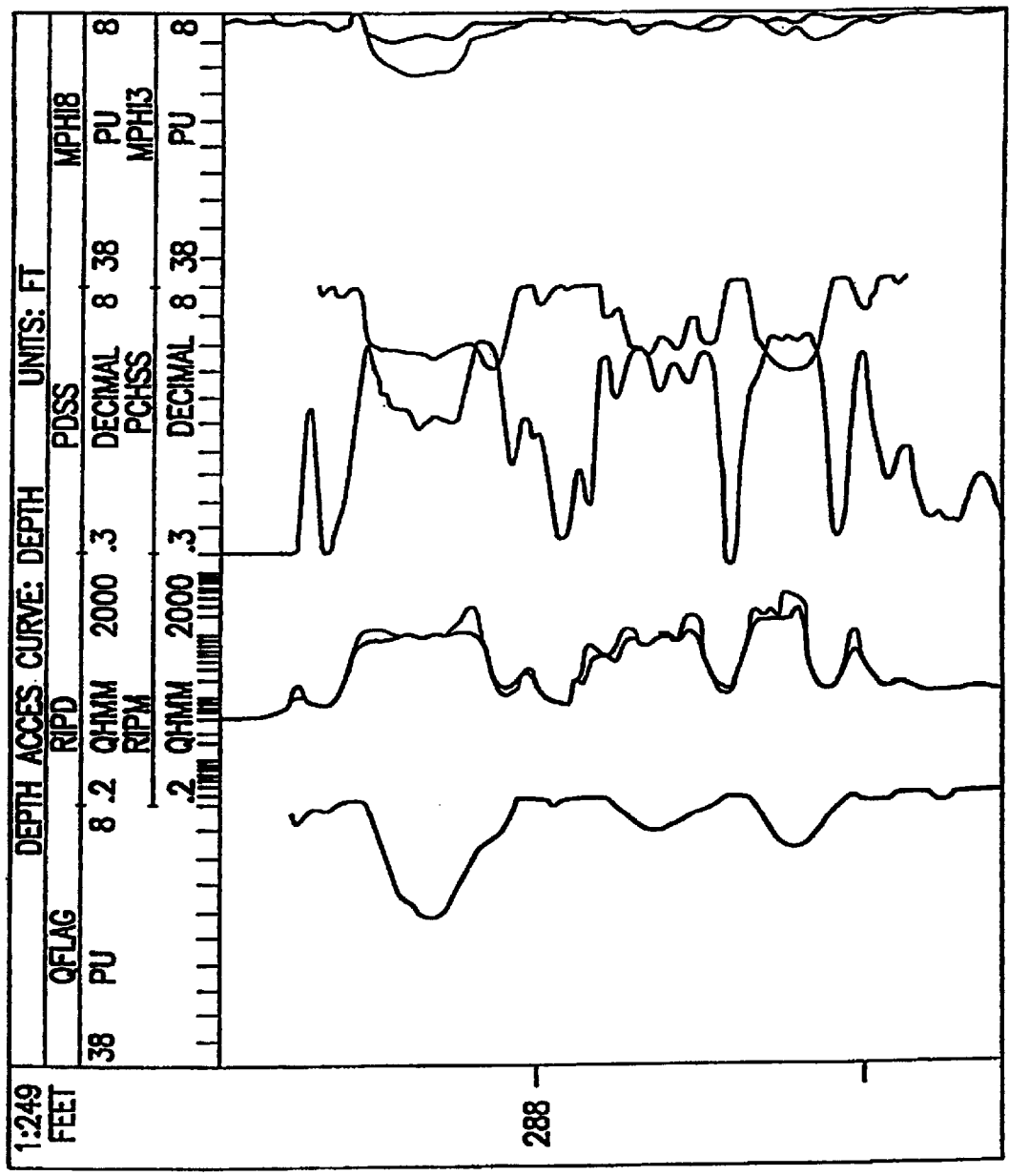
FIG. 11 shows logging data from an off-shore gas well at depth >10,000 ft.

Log results are shown in FIG. 11. For the example illustrated in FIG. 11 NMR data for recovery times of $TR_1=3$ s and $TR_2=8$ s were acquired in separate passes with a pulse-echo spacing $\tau=0.6$ ms. Both apparent NMR porosities are too low in the gas zone (shown in track 4). Complex echo sums and differences from these echo sets were computed. The sum had a constant phase of −2.1 rad, which was used to convert the difference signal to real-type values. Matched filters for the oil component:

$$HI_o=1.0, T_{1,o}=2000 \text{ ms}, T_{2,o}=1000 \text{ ms};$$

and for the gas component:

$$HI_g=0.6, T_{1,g}=6000 \text{ ms}, T_{2,g}^\dagger=60 \text{ ms};$$

were computed and applied to the data in a least-squares sense as described above. The oil-filter response was essentially zero (not shown), the gas-filter response is plotted in track 1.

Gas-corrected NMR porosity indicates that mud filtrate did not invade the sampling diameter (15" at a probe temperature of 100°C.), or that gas did backsaturate into the invaded zone. In either case, the results clearly indicate the value of hydrocarbon saturation measurements near the borehole wall.

Simulation Results for Embodiments Using Low Field Gradient

The NMR response can be computed by brute force from the Bloch Equations, or, more efficiently, by a Riemannian spherical affine projection onto the complex plane. The latter procedure ignores the effects of relaxation, which is appropriate here. Some results are shown in FIG. 13 and FIG. 14.

Figure 13A:
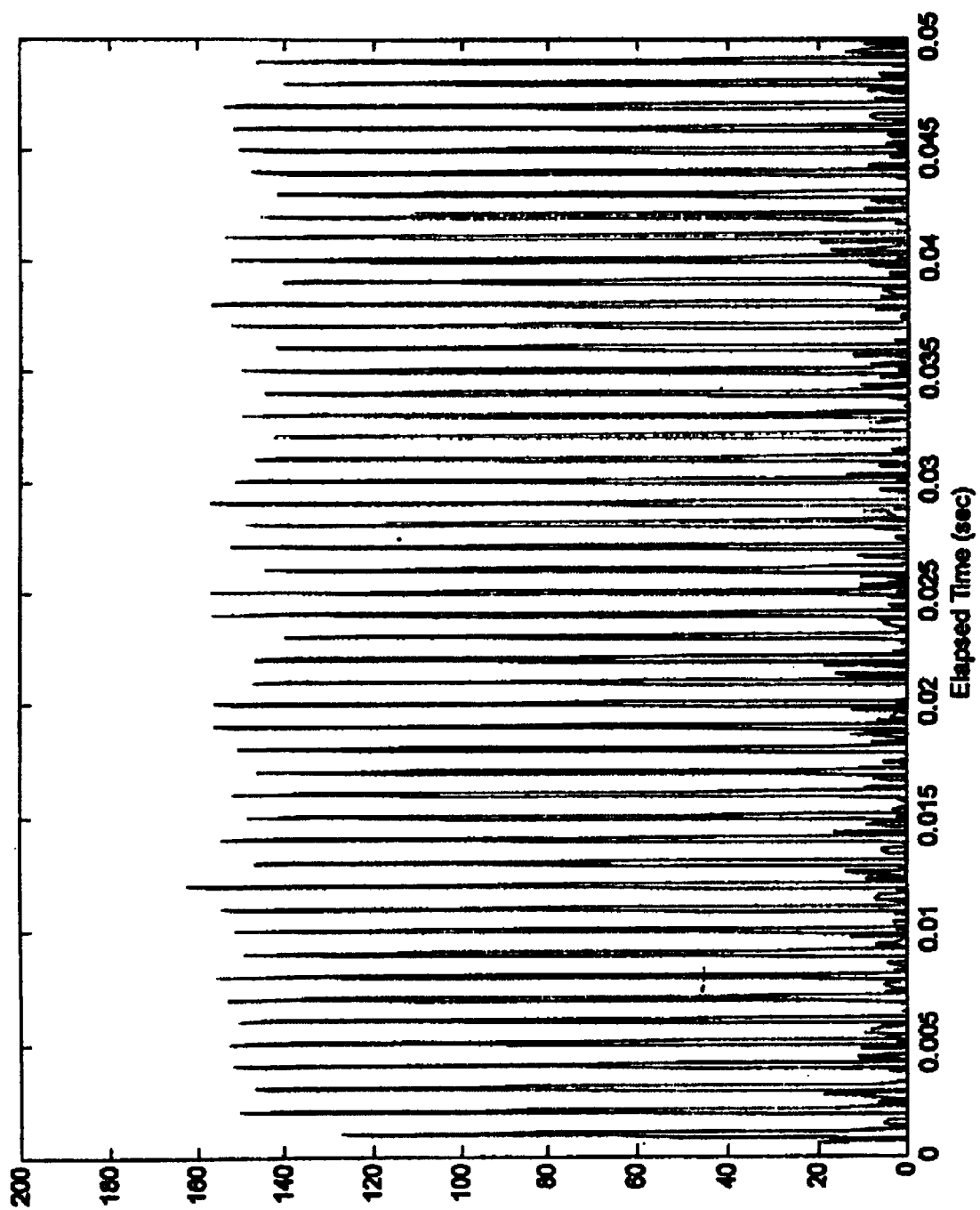
FIGS. 13A, 13B 14A and 14B illustrate simulation results showing computed echo amplitudes for the case of no diffusion and signal attenuation due to diffusion.
Figure 13B:
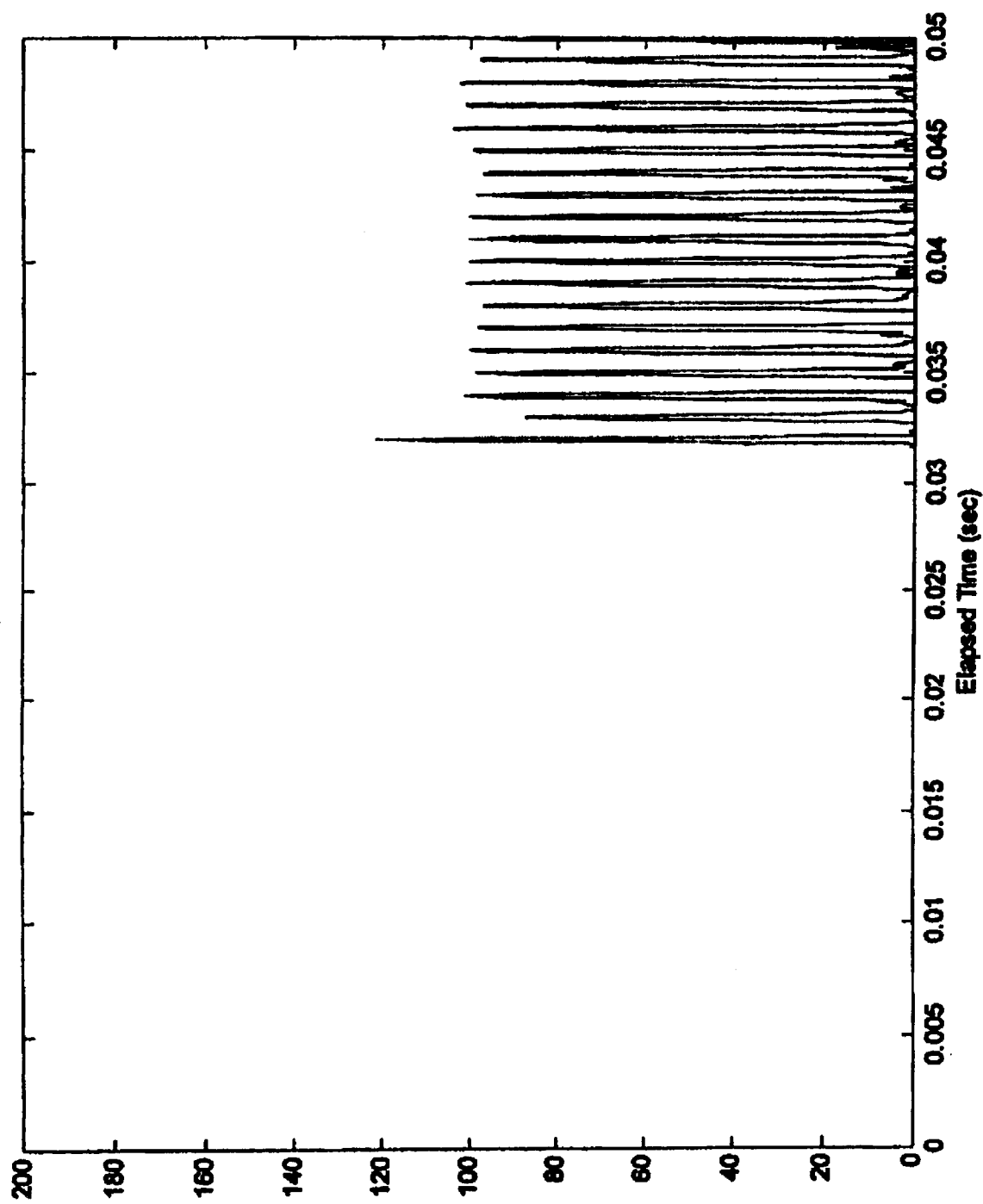

FIG. 13 treats the case of little or no diffusion. Switching TD to a value larger than TE results in loss of signal in echo 2 and onward. This effect can be understood by considering that echoes 2, 3, etc. contain both direct spin echoes, as well as indirect ("stimulated") echoes (See, for example, Goelman and Prammer: "The CPMG Pulse Sequence in Strong Magnetic Field Gradients With Applications to Oil-Well Logging," J. Magn. Reson. A 113 (March 1995), p. 11.) The significance of this observation is that in general calibrations must be performed separately for the case when TD=TE and TD>TE. Also, in order to recover signal-to-noise, preferably twice as many experiments per TD>TE value should be performed compared with the case when TD=TE.

The simulation results illustrated in the figure show computed echo amplitudes for the case of no diffusion. Only the first 50 echoes are shown, more typically 100–1000 echoes would be used in accordance with a preferred embodiment. The left diagram in FIG. 13 illustrates echo amplitudes for the case TD=TE=1 ms. The right diagram illustrates the case when TD=32 ms, TE=1 ms. Note that the first echo has the same amplitude as in the left figure, but all other echoes are attenuated. This is a result of the loss of stimulated echoes that are not carried over to the second echo and does not reflect attenuation due to diffusion. The amount of attenuation due to stimulated echo effects is predictable and can be calibrated in a preferred embodiment on a test sample.

Figure 14A:
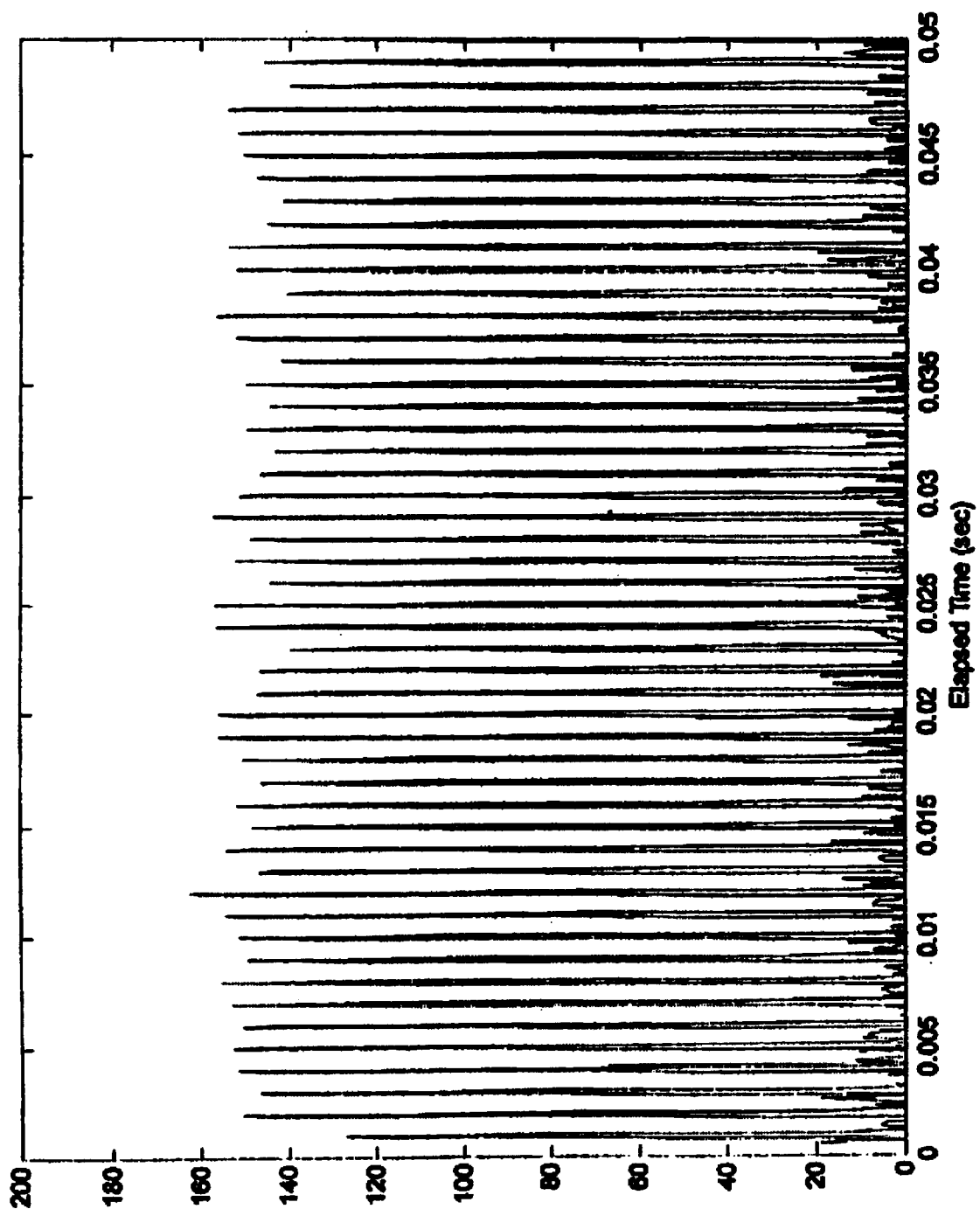
Figure 14B:
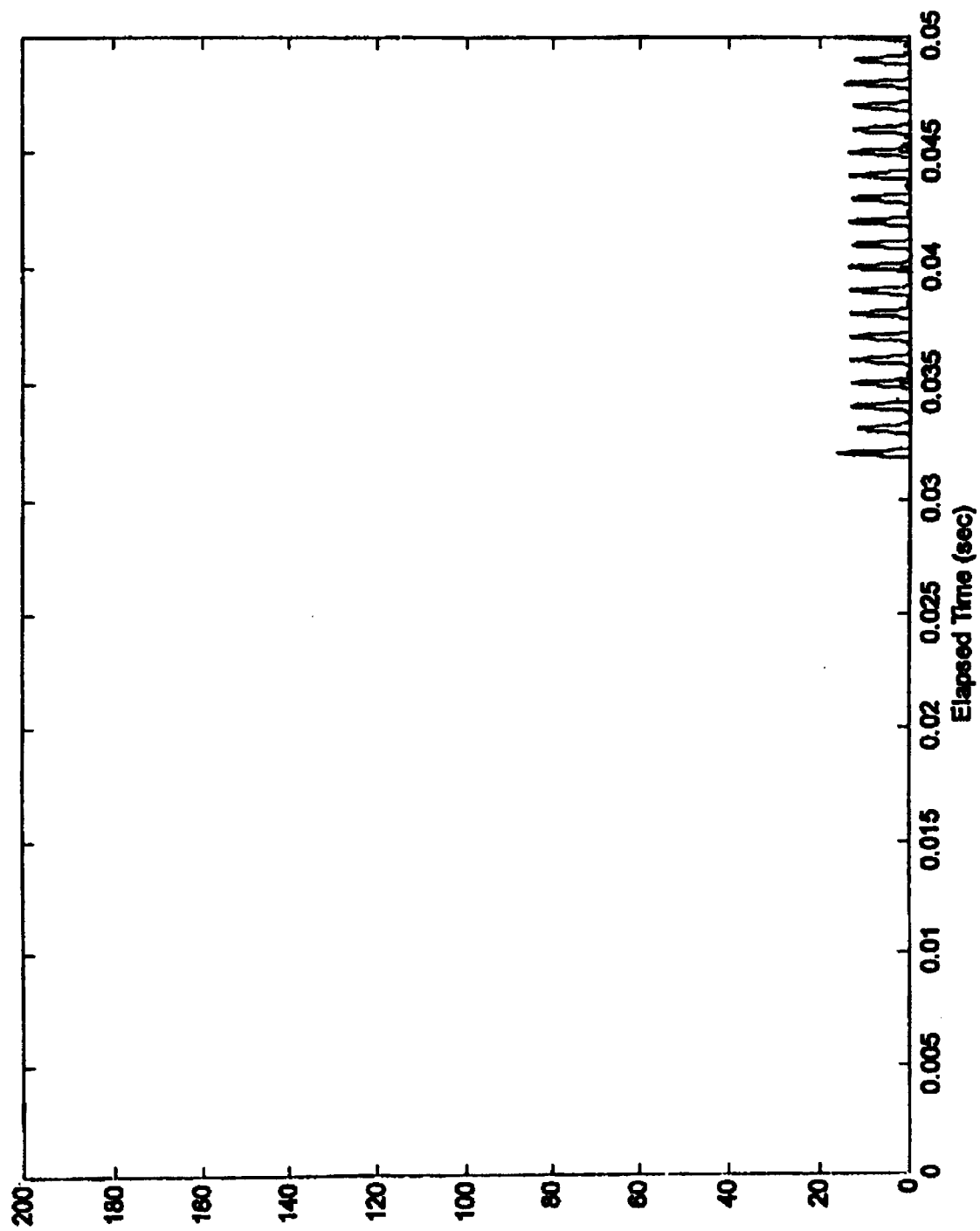

FIG. 14 shows the strong attenuation effect if fast diffusion is present. A (weak) gradient of 1 gauss/cm and a diffusion coefficient of $10^{-3}$cm$^2$/sec were assumed for these simulations. The simulation results show computed echo amplitudes for the case of rapid diffusion (D=$10^{-3}$ $cm^2/s$), typical of vapor phase under reservoir conditions). The left diagram illustrates echo amplitudes for the case TD=TE=1 ms. The right diagram illustrates the case when TD=32 ms, TE=1 ms. After accounting for the loss of stimulated echoes, the gas signal has been attenuated to 14% of its original value. The gas signal can be recovered in accordance with a preferred embodiment by individually fitting each echo train and comparing total amplitudes, or by subtracting the amplitudes of corresponding echoes. Thus, by subtracting echo-by-echo the right diagram from the left diagram (ignoring all echoes occurring at times less than TD), the gas phase signal can be isolated.

Appendix A provides listings of several NMR Simulation Programs in the Matlab programming language, which can be used in accordance with the present invention to perform the above-referred computations.

Processing

Job Planning. In accordance with the present invention job planning consists of estimating diffusivity values for gas, oil and free water and selecting appropriate TD and TE values based on forward-modeling of signal components to achieve maximum contrast between fluid phases. The simple calculation shown above is an example. Following is a brief description of a model-based linear inversion algorithm that can be used in accordance with a preferred embodiment for the forward modeling of signal components.

Model-based Linear Inversion Algorithm

Let a,b,c, . . . denote the indices for the free fluid components, e.g., gas, water and oil. Let also $S_i$ (i=a,b,c . . . ) denote a signal component and let $V_i$ (i=a,b,c . . . ) be the volume occupied by a fluid component. S and V are related as follows:

$$S_i = K/T \times HI_i \times P_i \times V_i.$$

where

K is a calibration constant containing the system gain, the gyromagnetic ratio, the operating frequency, etc.; T is the absolute temperature;

$HI_i$ is the hydrogen index (i.e., hydrogen density relative to water) of the i-th signal component;

$P_i$ is a component-specific polarization term, typically of the form $(1-\exp(-Tw/T1_i))$, where Tw is the pre-measurement wait time (polarization time) and $T1_i$ is the T1 time constant of the i-th component.

Measurements are made with at least three different values for TD. In a specific example: TD=1, 32 and 70 ms.

The echo spacing TE is held constant (example: TE=1 ms). All echoes occurring before 70 ms are ignored to eliminate the influence of fast-decaying components from water or oil phases. A relatively short acquisition window is selected (example: 10–100 ms). Within this time window, the inherent T2 decay is small for all free-fluid components and all echoes within the time window can be summed and averaged. This step improves the SNR by a factor of 3–10. The net result are three numbers, representing the averaged observed signal amplitude after 70 ms under the conditions of TD=1, 32 and 70 ms. Let $A_j$, (j=1,2,3, . . . ) be these numbers. The signals $S_i$ and the measured amplitudes $A_j$ are related to each other as follows:

$A_j = M_{ji} S_i$, or, in explicit notation:

$$\begin{bmatrix} A_1 \\ A_2 \\ A_3 \\ \ldots \end{bmatrix} = \begin{bmatrix} M_{1a} & M_{1b} & M_{1c} & \ldots \\ M_{2a} & M_{2b} & M_{2c} & \ldots \\ M_{3a} & M_{3b} & M_{3c} & \ldots \\ \ldots & \ldots & \ldots & \ldots \end{bmatrix} \times \begin{bmatrix} S_a \\ S_b \\ S_c \\ \ldots \end{bmatrix}$$

The matrix elements $M_{ji}$ encode the response of each fluid component to a specific value of TD. There are given by $$M_{ji} = \exp(-1/12(\gamma^2 G^2 TD_j^3 D_i)).$$

$\gamma$ is the gyromagnetic ratio (2 $\pi$4258 sec$^{-1}$/gauss), G is the field gradient, and $D_i$ is the diffusivity of the i-th component. Continuing with the example: G=1 gauss/cm, and $D_1 = 10^{-3}$ cm$^2$/s for the vapor (gas) phase,
$D_2 = 10^{-4}$ cm$^2$/s for the free-water phase, and
$D_3 = 10^{-5}$ cm$^2$/s for the oil phase.
Then:

$$M = \exp(-1/12 \times \gamma^2 \times G^2 \times [\, 0.001^3 \quad 0.032^3 \quad 0.070^3 \,]^T \times$$
$$[\, 10^{-3} \quad 10^{-4} \quad 10^{-5} \,])$$
$$= \begin{matrix} 0.9999 & 1.0000 & 1.0000 \\ 0.1416 & 0.8225 & 0.9806 \\ 0.0000 & 0.1293 & 0.8150 \end{matrix}$$

The inverse of this matrix is:

$$M^{-1} = \begin{matrix} 1.2176 & -1.5362 & 0.3544 \\ -0.2586 & 1.8257 & -1.8795 \\ 0.0410 & -0.2896 & 1.5251 \end{matrix}$$

The individual signal components are given by:

$$S_i = (M^{-1})_{ij} A_j$$

And, finally, the fluid volumes themselves:

$$V_i = (K/T \times HI_i P_i \times V_i)^{-1} \times S_i.$$

With proper calibration factors, these volumes can be expressed in porosity units or saturation fractions, i.e. relative to total porosity.

Postprocessing. In accordance with a preferred embodiment, in postprocessing, calibrations are applied to eliminate stimulated echo effects that distort echo amplitudes. Next, the echo trains for various TD values are processed either simultaneously or in pairs. If processed in pairs, only the common time windows (from the longest TD interval onward) are considered. The subtraction of corresponding echoes enhances a particular fluid phase: the gas phase between the two shortest TD values; the water phase between the next TD pair, and the oil phase from the longest TD value only without subtraction. Lastly, correction values are applied that account for (a) incomplete polarization, (b) incomplete suppression by diffusion, and (c) hydrogen density.

Figure 15A:
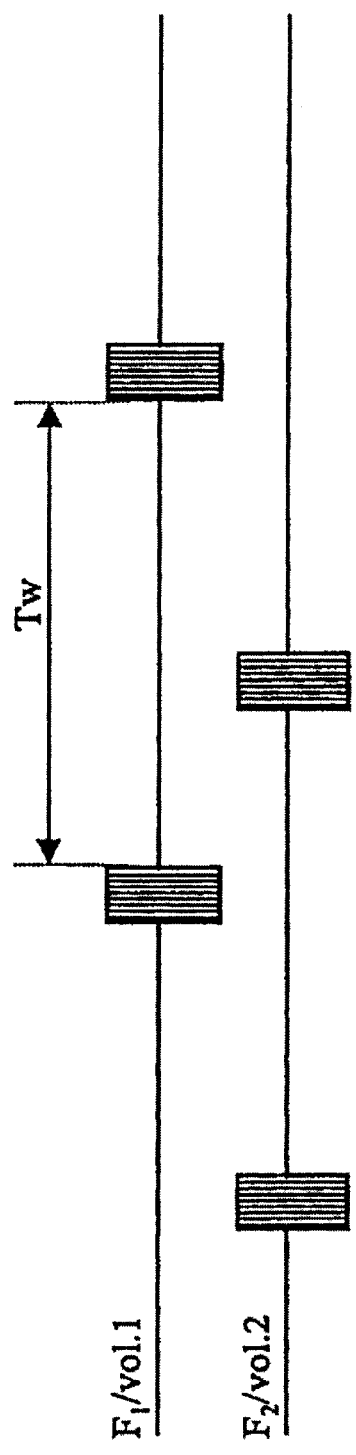
FIGS. 15A and 15B illustrate a multi-frequency TD/TE pulse sequence in accordance with a preferred embodiment.
Figure 15B:
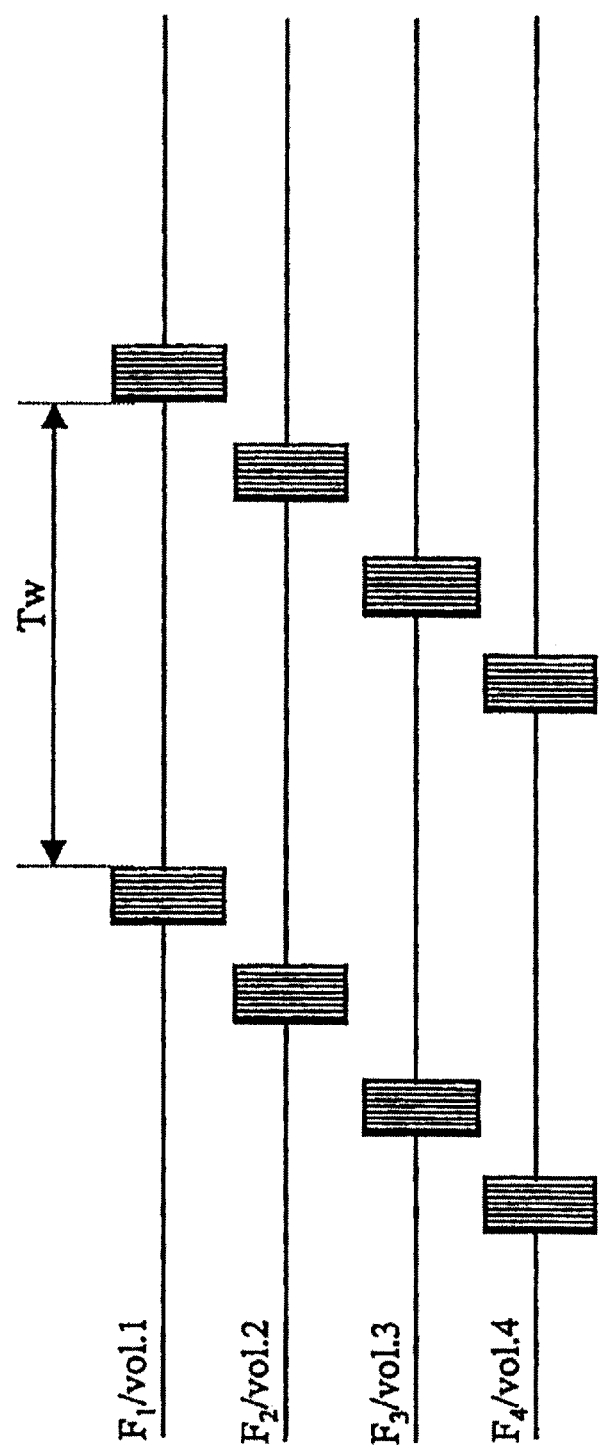

The low-field gradient processing method in accordance with the present invention can be further combined with the frequency hopping method using variable wait times. FIG. 15 is an illustration of a multi-frequency TD/TE pulse sequence. Each box in FIG. 15 represents a TD/TE sequence. In a preferred embodiment, the TD parameter is systematically cycled through all of its values. The wait time Tw is kept constant and is typically in the range of 8 to 12 seconds, although other values may be used in specific embodiments. FIG. 15 A shows an implementation of the method of the present invention using a modified TD/TE pulse sequence for two frequencies (i.e., two sensitive volumes). FIG. 15B illustrates the use of the modified pulse sequence in the case of four operating frequencies (sensitive volumes). Signal components with long $T_1$ relaxation values can be selectively attenuated by choosing wait times between CPMG and modified CPMG trains that are short compared to $T_1$.

APPENDIX A

```
%    CPMG.M - - - CPMG sequence
%
%    NMR Simulation Program.
%
%       © Copyright, M. G. Prammer, NUMAR Corp., 1991, 1992, 1993.
%    Modification History:
%       Oct. 1991, MGP, Written.
%       Jul. 1992, MGP, modified pulsim.
%
%%%%%%%%%%%%%%%%%%%%%%%% experimental parameters
%%%%%%%%%%%%%%%%%%%%%%%%%%%%%%
     echo on;
     T2 = 1e6;          % T2 sec        Assumed true T2
     TE = 1e-3;         % TE sec        Echo time
     NE = 50;           % NE            Number of echoes
     t90 = 100e-6;      % t90 sec       90-degree pulse width
     t180 = 160e-6;     % t180 sec      180-degree pulse width
     AT = TE-t180;      % AT sec        Acquisition time
     dt = 20e-6;        % dt sec        Dwell time
     A = 1/(2*t180);    % A Hz          Pulse amplitude
     fmin = -5000;      % fmin Hz       Leftmost freq sample
     fmax = 5000;       % fmax Hz       Rightmost freq sample
     df = 40;           % df Hz         Frequency resolution
     fjitter = 10;                      % fjitter Hz    Random frequency jitter
     figure(1);
     echo off;
%%%%%%%%%%%%%%%%%%%%%%%%%%%%%%%%%%%%%%%%%%%%%
%%%%%%%%%%%%%%%%%%%%%%%%%%%%%%%%%%%%%%
     t=0:dt:AT;              % create acquisition time axis
     f=fmin:df:fmax;         % create frequency axis
     [dum,NF]=size(f);       % NF . . . no of frequency points
     sx=[ ];                 % real channel signal
     sy=[ ];                 % imaginary channel signal
% establish equilibrium
     mx=zeros(size(f));
     my=zeros(size(f));
     mz=ones(size(f));
% 90 pulse; phase = 90
     [mx,my,mz]=pulsim(j*A,t90,f,mx,my,mz);
     [mx,my,mz]=evolve(T2,t90+(TE-t90-t180)/2,f,mx,my,mz);    %!!!
   for nr=1:NE,
     %fprintf('Echo %.0f\n',nr*1.0);
% 180 pulse; phase = 0
     [mx,my,mz]=pulsim(A,t180,f,mx,my,mz);
     [tmpx,tmpy]=observe(dt,AT,f,mx,my,mz);        % compute response
     [mx,my,mz]=evolve(T2,TE-t180,f,mx,my,mz);     % evolve
     [mx1,my1,mz1]=evolve(T2,(TE-t180)/2,f,mx,my,mz);  % echo profile
     sx=[sx ; tmpx]; sy=[sy ; tmpy];
     s=sqrt(sx.^2+sy.^2);
     plot(t,sx); grid;
     xlabel('Time in sec after pi pulse.');
        drawnow;
% introduce frequency jitter to mask numerical discretization
        f = f+fjitter*randn(size(f));
     end
% create entire timeline
tall=[ ];
for nr=1:NE,
     tall=[tall nr*TE+(-AT/2:dt:AT/2)];
end
% plot entire train
tmp=sx'; sxall=tmp(:);
figure(2); plot(tall,sxall);
axis([0 0.05 0 200]);
xlabel('Elapsed Time (sec)');
%    TDCPMG.M - - - Simulate DElayed CPMG sequence
%
%       NMR Simulation Program.
```

APPENDIX A-continued

```
%
%   Modification History:
%       May 2001
%
%%%%%%%%%%%%%%%%%%%%%%%%% experimental parameters
%%%%%%%%%%%%%%%%%%%%%%%%%%%%%%%%
        echo on;
        T2 = 1e6;         % T2 sec      Assumed true T2
        TE = 1e-3;        % TE sec      Echo time
        TD = 32e-3;       % TD sec      Delay time from pi/2 to 1st echo
        NE = 50;          % NE          Number of echoes
        t90 = 100e-6;     % t90 sec     90-degree pulse width
        t180 = 160e-6;    % t180 sec    180-degree pulse width
        AT = TE-t180;     % AT sec      Acquisition time
        dt = 20e-6;       % dt sec      Dwell time
        A = 1/(2*t180);   % A Hz        Pulse amplitude
        fmin = -5000;     % fmin Hz     Leftmost freq sample
        fmax = 5000;      % fmax Hz     Rightmost freq sample
        df = 40;          % df Hz       Frequency resolution
        fjitter = 10;                   % fjitter Hz    Random frequency jitter
        figure(1);
        echo off;
%%%%%%%%%%%%%%%%%%%%%%%%%%%%%%%%%%%%%%%%%
%%%%%%%%%%%%%%%%%%%%%%%%%%%%%%%%%
        t=0:dt:AT;           % create acquisition time axis
        f=fmin:df:fmax;        % create frequency axis
        [dum,NF]=size(f);       % NF . . . no of frequency points
        sx=[];              % real channel signal
        sy=[];              % imaginary channel signal
% establish equilibrium
        mx=zeros(size(f));
        my=zeros(size(f));
        mz=ones(size(f));
% 90 pulse; phase = 90
        [mx,my,mz]=pulsim(j*A,t90,f,mx,my,mz);
% TD/2 - pi pulse (phase=????)
        [mx,my,mz]=evolve(T2,t90+(TD-t90-t180)/2,f,mx,my,mz);
        [mx,my,mz]=pulsim(-A,t180,f,mx,my,mz);
% TD/2 - first echo
        [mmx,mmy,mmz]=evolve(T2,(TD-t180-AT)/2,f,mx,my,mz);
        [tmpx,tmpy]=observe(dt,At,f,mmx,mmy,mmz);         % compute response
        sx=[sx ; tmpx]; sy=[sy ; tmpy];
        s=sqrt(sx.^2+sy.^2);
        plot(t,sx); grid;
        xlabel('Time in sec after pi pulse.');
                drawnow;
%backtrack to right after 1st pulse and evolve
        [mx,my,mz]=evolve(T2,TD./2+TE./2-t180,f,mx,my,mz);
        for nr=2:NE,
        %fprintf('Echo %.0f\n',nr*1.0);
% pi pulse; phase = 0
        [mx,my,mz]=pulsim(A,t180,f,mx,my,mz);
        [tmpx,tmpy]=observe(dt,AT,f,mx,my,mz);            % compute response
        [mx,my,mz]=evolve(T2,TE-t180,f,mx,my,mz);         % evolve
        [mx1,my1,mz1]=evolve(T2,(TE-t180)/2,f,mx,my,mz);  % echo profile
        sx=[sx ; tmpx]; sy=[sy ; tmpy];
        s=sqrt(sx.^2+sy.^2);
        plot(t,sx); grid;
        xlabel('Time in sec after pi pulse.');
        drawnow;
% introduce frequency jitter to mask numerical discretization
        f = f+fjitter*randn(size(f));
    end
% create entire timeline
tall=[];
for nr=1:NE,
    tall=[tall TD+(nr-1)*TE+(-AT/2:dt:AT/2)];
end
% plot entire train
tmp=sx'; sxall=tmp(:);
figure(2); plot(tall,sxall);
axis([0 0.05 0 200]);
xlabel('Elapsed Time (sec)');
%*************************************************
function [mx,my,mz] = pulsim( amp, tau, f, mx0, my0, mz0 )
%
%       © Copyright, M. G. Prammer, NUMAR Corp., 1991.
%
%   PULSIM - - - calculate hard pulse response.
```

APPENDIX A-continued

```
%       [mx,my,mz] = pulsim( amp, tau, f, mx0, my0, mz0)
%           amp ... real or complex pulse amplitude in Hz.
%           tau ... pulse duration in sec.
%           f ... frequency sampling points in Hz.
%           mx,my,mz ... cartesian magnetization components.
%       Method: Riemannian spherical affine projection onto
%       complex plane, followed by complex transform. Yao, JMR.
%       Fails for Mz<=(-1+1e-16). Written by MGP, Oct. 1991.
%       Frequency sign corrected for right hand reference frame. MGP, 12/17/91.
M=sqrt(mx0.^2+my0.^2+mz0.^2);   % magnetization vector length
mx0=mx0./M; my0=my0./M; mz0=mz0./M; % normalize
Om = sqrt(abs(amp).^2+f.^2);    % effective rotation freq in Hz
ct = -f./Om;            % cos of rotation angle theta +++MGP (-).
st = sqrt(1-ct.^2);     % sin of rotation angle theta
ep = amp./abs(amp);     % phasor for argument of amp
W = (mx0+j*my0)./(1+mz0).*conj(ep);% project onto complex plane
cotom = j./tan(Om*tau*pi);  % needed for rotation
W = ep.*( st-(ct-cotom).*W)./( ct+cotom+st.*W); % perform rotation
wf = real( W.*conj(W));     % backtransform
mx = M.*real((W+conj(W))./ (1+wf));
my = M.*real((W-conj(W))./(j*(1+wf)));
mz = M.*(1-wf)./(1+wf);
%*************************************************************
function [mx,my,mz] = evolve( T2, tau, f, mx0, my0, mz0)
%
%           © Copyright, M. G. Prammer, NUMAR Corp., 1991.
%
%       EVOLVE - - - evolve spin system in time.
%       [mx,my,mz] = evolve( T2, tau, f, mx0, my0, mz0)
W = (mx0+j*my0).*exp(-tau/T2 + j*2*pi*tau.*f);
mx = real(W);
my = imag(W);
mz = mz0;
% if any(isnan(mx)),
%  fprintf('\nError in EVOLVE - - - ');
%  keyboard;
% end
%*************************************************************
function [sx,sy] = observe( dt, AT, f, mx0, my0, mz0)
%
%           © Copyright, M. G. Prammer, NUMAR Corp., 1991.
%
%       OBSERVE - - - calculate observable signal.
%       [sx,sy] = observe( dt, AT, f, mx0, my0, mz0)
%           dt ... dwell time,
%           AT ... (total) acquisition time,
%           f ... frequency axis,
%           mx, my, mz ... magnetization before acquisition (NOT updated).
%
%t=0:dt:AT;
%W=(mx0+j*my0).*exp(j*2*pi*t'*f);
%sx=[]; sy=[];
%[dum,nt]=size(t);
%for k=1:nt,
%   sx=[sx sum(real(W(k,:)))];
%   sy=[sy sum(imag(W(k,:)))];
%end
sx=[]; sy=[];
W0=mx0+j*my0;
J2PI=j*2*pi;
for t=0:dt:AT,
   W=W0.*exp(J2PI*t.*f);
   mx=real(W); my=imag(W);
   sx=[sx sum(mx)]; sy=[sy sum(my)];
end
```

While the invention has been described with reference to a preferred embodiment, it—will be appreciated by those of ordinary skill in the art that modifications can be made to the structure and form of the invention without departing from its spirit and scope which is defined in the following claims.

What is claimed is:

1. A method for making nuclear magnetic resonance (NMR) measurements of a geologic formation using a NMR logging tool, comprising the steps of:

(a) providing a static magnetic field in a volume of said formation;

(b) applying a modified CPMG pulse sequence according to the expression:

$$W_i - \pi/2 - TD_j/2 - \pi - TD_j/2 - \text{echo} - [TE/2 - \pi - TE/2 - \text{echo}]_k$$

where $W_i$ is a variable delay with $i \geq 1$; $TD_j$ is variable echo spacing, $j \geq 1$; $TE/2$ is the Carr-Purcell echo spacing, $TD_j > TE$; $k = 1, \ldots, N$; and (c) measuring the induced NMR echo signals.

2. The method of claim 1 further comprising the step of processing the induced NMR echo signals to derive petrophysical properties of the formation.

3. The method of claim 1 further comprising the step of selecting the variable echo spacing $TD_j$ such that the application of the modified CPMG pulse sequence causes the loss of pre-determined fast diffusion components of the measured NMR echo signals.

4. The method of claim 3, wherein $TD_j$ is selected to cause the loss of signals associated with the gas phase.

5. The method of claim 3, wherein $TD_j$ is selected to cause the loss of signals associated with the gas phase and the water phase.

6. The method of claim 1, wherein the TE echo spacing is relatively short.

7. The method of claim 6, wherein the TE echo spacing is about 1 ms.

8. The method of claim 1, wherein j>2 and the $TD_j$ are different.

9. The method of claim 1, wherein $TD_1$=5 ms.

10. The method of claim 1 further comprising the step of pairwise subtracting NMR echo signals associated with different $TD_j$'s.

11. The method of claim 7 further comprising the step of separating the gas, oil and water signal components.

12. A method for making nuclear magnetic resonance (NMR) measurements of a geologic formation, comprising the steps of:
   (a) providing a static magnetic field in a volume of said formation;
   (b) applying oscillating magnetic fields according to at least one modified CPMG pulse sequence characterized by having at least one first echo spacing TD and a second echo spacing TE; wherein the at least one first echo spacing TD is selected to correspond to diffusion characteristics of fluids in the formation and cause corresponding amplitude loss in induced NMR signals, and TE is relatively short, such that diffusion in the corresponding induced NMR echo signals is substantially negligible;
   (c) measuring the induced NMR echo signals;
   (d) determining the amount of amplitude loss resulting from at least one TD interval;
   (e) computing diffusion properties of fluids in the formation based on the determined amplitude loss.

13. The method of claim 12, wherein the modified CPMG sequence is repeated with at least one first echo spacing TD=TE and at least one first echo spacing TD≠TE.

14. The method of claim 12 further comprising the step of processing the induced NMR echo signals to derive petrophysical properties of the formation.

15. The method of claim 12, wherein at least one first TD is selected to cause the loss of signals associated with the gas phase.

16. The method of claim 12, wherein TD is selected to cause the loss of signals associated with the gas phase and the water phase.

17. The method of claim 12, wherein the TE echo spacing is about 1 ms.

18. The method of claim 12, wherein at least two different TD first echo spacings are used.

19. The method of claim 12, wherein a first echo spacing $TD_1$=TE and first echo spacing $TD_2$=5 ms.

20. The method of claim 12 further comprising the step of pairwise subtracting NMR echo signals associated with different TD's to separate different fluid phases present in the formation.

21. The method of claim 20 further comprising the step of separating gas, oil and water signal components present in the formation.

22. The method of claim 12 further comprising the step of estimating diffusivity values for gas, water and oil phases in the formation, and selecting values for the TD and TE echo spacings based on the estimated diffusivity values.

23. The method of claim 22, wherein the selection of values for the TD and TE echo spacings is based on forward-modeling of signal components to achieve maximum contrast between fluid phases.

24. The method of claim 12 further comprising the step of applying calibrations to eliminate stimulated echo effects that distort echo amplitudes.

25. The method of claim 12, wherein in step (e) echo trains for different TD values are processed either simultaneously or in pairs.

26. The method of claim 25, wherein echo trains for different TD values are processed in pairs, and only common time windows from the longest TD interval onward are considered in the step of processing.

27. The method of claim 26 further comprising the step of subtracting of corresponding echoes to enhance a particular fluid phase.

28. The method of claim 27, wherein the gas phase is enhanced by subtracting the two shortest TD values; the water phase between the next TD pair, and the oil phase from the longest TD value only without subtraction.

29. The method of claim 12, further comprising applying correction values that account for (a) incomplete polarization, (b) incomplete suppression by diffusion, and (c) hydrogen density.

30. A system for making nuclear magnetic resonance (NMR) measurements of a geologic formation, comprising:
   (a) means for providing a static magnetic field in a volume of said formation;
   (b) means for applying oscillating magnetic fields according to at least one modified CPMG pulse sequence characterized by having at least one first echo spacing TD and a second echo spacing TE; wherein the at least one first echo spacing TD is selected to correspond to diffusion characteristics of fluids in the formation and cause corresponding amplitude loss in induced NMR signals, and TE is relatively short, such that diffusion in the corresponding induced NMR echo signals is substantially negligible;
   (c) means for measuring the induced NMR echo signals;
   (d) means for determining the amount of amplitude loss resulting from at least one TD interval; and
   (e) means for computing diffusion properties of fluids in the formation based on the determined amplitude loss.

* * * * *